(12) United States Patent
Ono et al.

(10) Patent No.: US 8,908,022 B2
(45) Date of Patent: Dec. 9, 2014

(54) IMAGING APPARATUS

(71) Applicant: Olympus Medical Systems Corp., Tokyo (JP)

(72) Inventors: Wataru Ono, Hachioji (JP); Hidenori Hashimoto, Hachioji (JP); Hirohiko Matsuzawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/721,873

(22) Filed: Dec. 20, 2012

(65) Prior Publication Data
US 2013/0169775 A1    Jul. 4, 2013

Related U.S. Application Data

(63) Continuation of application No. PCT/JP2011/078904, filed on Dec. 14, 2011.

(30) Foreign Application Priority Data

Dec. 14, 2010  (JP) ................................. 2010-278035

(51) Int. Cl.
| | | |
|---|---|---|
| A62B 1/04 | (2006.01) | |
| A61B 1/00 | (2006.01) | |
| H04N 5/225 | (2006.01) | |
| H04N 5/374 | (2011.01) | |
| A61B 1/12 | (2006.01) | |

(52) U.S. Cl.
CPC .......... *A61B 1/00009* (2013.01); *H04N 5/2251* (2013.01); *A61B 1/00006* (2013.01); *H04N 5/374* (2013.01); *A61B 1/128* (2013.01); *H04N 2005/2255* (2013.01)
USPC ................... 348/68; 348/45; 348/69; 348/77

(58) Field of Classification Search
CPC ........ A61B 1/00009; A61B 1/05; A61B 1/04; A61B 1/041; A61B 1/00006; A61B 1/128; A61B 1/0661; H04N 5/2256; H04N 5/2354; H04N 2005/2255; H04N 5/217; H04N 5/23203; H04N 7/183; H04N 5/335

USPC ................... 600/101, 109, 114, 118; 348/45, 348/62–161
See application file for complete search history.

(56) References Cited

U.S. PATENT DOCUMENTS

| 5,374,953 A | 12/1994 | Sasaki et al. |
|---|---|---|
| 6,511,422 B1 | 1/2003 | Chatenever |

(Continued)

FOREIGN PATENT DOCUMENTS

| EP | 1 894 517 A2 | 3/2008 |
|---|---|---|
| JP | 63-139483 | 6/1988 |

(Continued)

OTHER PUBLICATIONS

International Search Report dated Jan. 24, 2012 issued in PCT/JP2011/078904.

(Continued)

*Primary Examiner* — Sath V Perungavoor
*Assistant Examiner* — Nathnael Aynalem
(74) *Attorney, Agent, or Firm* — Scully, Scott, Murphy & Presser, PC

(57) ABSTRACT

An endoscope system according to the present invention includes: a CMOS imaging element; a timing generator and an AFE unit that are provided on a board connected to a light receiving unit and reads pixel information by causing the pixel information to be output from a pixel designated as a target to be read in the CMOS imaging element; a control circuit that is provided on the board and controls a pixel information output process by a light receiving unit and a pixel information reading process by the timing generator and the AFE unit; and an abnormality determining unit that determines whether there is an abnormality in the pixel information read by the timing generator and the AFE unit and outputs, to the control circuit, a notification signal for causing the control circuit to execute control on an occurrence of the abnormality.

10 Claims, 15 Drawing Sheets

(56) References Cited

U.S. PATENT DOCUMENTS

| | | | |
|---|---|---|---|
| 6,724,418 B1 * | 4/2004 | Takahashi | 348/65 |
| 6,753,901 B1 * | 6/2004 | Takahashi et al. | 348/65 |
| 6,796,939 B1 * | 9/2004 | Hirata et al. | 600/179 |
| 8,199,235 B2 * | 6/2012 | Okita et al. | 348/301 |
| 8,514,278 B2 * | 8/2013 | Karpen et al. | 348/80 |
| 8,517,920 B2 * | 8/2013 | Tani et al. | 600/118 |
| 2004/0044275 A1 | 3/2004 | Hakamata | |
| 2009/0213212 A1 * | 8/2009 | Nakamura | 348/65 |
| 2009/0290018 A1 * | 11/2009 | Abe | 348/76 |
| 2010/0063352 A1 * | 3/2010 | Matsuura | 600/103 |
| 2010/0261961 A1 | 10/2010 | Scott et al. | |

FOREIGN PATENT DOCUMENTS

| | | |
|---|---|---|
| JP | 2003-229994 | 8/2003 |
| JP | 2008-118263 | 5/2008 |
| JP | 2008-177735 | 7/2008 |
| JP | 2009-192358 | 8/2009 |
| JP | 2009-201540 | 9/2009 |
| JP | 2010-119461 | 6/2010 |
| WO | WO 01/10291 A1 | 2/2001 |

OTHER PUBLICATIONS

Extended Supplementary European Search Report dated Oct. 11, 2013 in counterpart European Patent Application No. 11848259.5.

* cited by examiner (1) NORMAL (HIGH RESOLUTION)

(2) ABNORMAL (THINNING-OUT)

US 8,908,022 B2

IMAGING APPARATUS

CROSS REFERENCES TO RELATED APPLICATIONS

This application is a continuation of PCT international application Ser. No. PCT/JP2011/078904 filed on Dec. 14, 2011, which designates the United States and claims the benefit of priority from Japanese patent application No. 2010-278035 filed on Dec. 14, 2010, and the entire contents of the PCT international application and the Japanese patent application are incorporated herein by reference.

BACKGROUND OF THE INVENTION

1. Field of the Invention

The present invention relates to an imaging apparatus including an imaging unit that is able to output, as pixel information, an electric signal that has been photoelectrically converted from a pixel arbitrarily designated as a target to be read from among a plurality of pixels for imaging.

2. Description of the Related Art

Conventionally, in the field of medicine, endoscope systems are used to observe inside organs of subjects. In an endoscope system, in general, an elongated flexible insertion portion is inserted into a body cavity of a subject, such as a patient, white light is irradiated onto body tissues in the body cavity through the insertion portion that has been inserted, and light reflected therefrom is received by an imaging unit at a distal end of the insertion portion, to capture an in-vivo image. The captured body image is displayed on a monitor of the endoscope system. A user, such as a doctor, observes inside the body cavity of the subject using the in-vivo image displayed on the monitor of the endoscope system.

In such an endoscope system, an imaging element is built in at the distal end of the insertion portion and transmits an electric signal that has been photoelectrically converted as an image signal to a signal processing device, and the signal processing device processes the transmitted signal, to thereby display an image captured by the imaging element and observe inside a body. The imaging element at the distal end of the insertion portion and the signal processing device are connected to each other by an assembled cable bundled of a plurality of signal lines in order to transmit the image signal, transmit a clock signal, and supply driving power to the imaging element (for example, see Japanese Patent Application Laid-open No. 2009-192358).

SUMMARY OF THE INVENTION

An imaging apparatus according to an aspect of the present invention includes: an imaging unit that is able to output, as pixel information, an electric signal that has been photoelectrically converted from a pixel arbitrarily designated as a target to be read from among a plurality of pixels for imaging; a reading unit that is provided on a board mounted with the imaging unit and reads pixel information from the pixel instructed as the target to be read in the imaging unit; an imaging-side control unit that is provided on the board and controls a pixel information output process by the imaging unit and a pixel information reading process by the reading unit; an image processing unit that generates an image from the pixel information read by the reading unit; a display unit that displays the image generated by the image processing unit; a setting unit is able to arbitrarily set the pixel to be read in the imaging unit; a control unit that changes the pixel to be read based on the setting by the setting unit; an abnormality determining unit that determines whether there is an abnormality in the pixel information read by the reading unit and outputs, upon determining that there is the abnormality in the pixel information read by the reading unit, to the imaging-side control unit, a notification signal for causing the imaging-side control unit to execute control on occurrence of the abnormality; and a light irradiating unit that irradiates light to an object, wherein the control unit controls, when the abnormality determining unit determines that there is the abnormality in the pixel information read by the reading unit, the light irradiating unit to reduce an amount of light irradiated by the light irradiating unit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
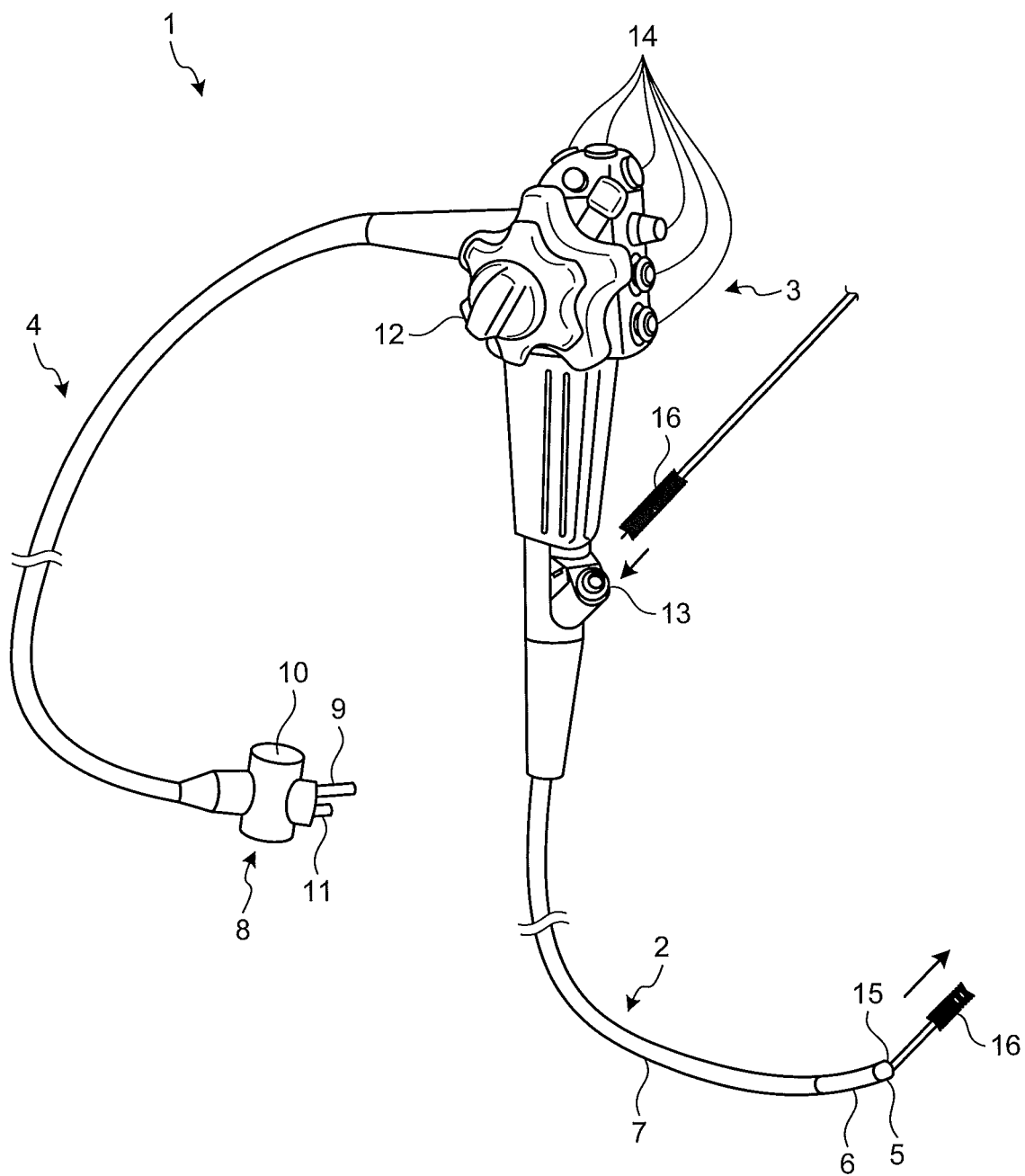
FIG. 1 is a diagram illustrating the schematic structure of an endoscopic portion according to a first embodiment.

Hereinafter, a medical endoscopic system according to an embodiment of the invention will be described which includes an imaging element at the distal end of an insertion portion, captures the image of the body cavity of a subject, such as a patient, and displays the captured image. The invention is not limited by this embodiment. In the drawings, the same components are denoted by the same reference numerals. In addition, the drawings are illustrative and it is noted that, for example, the relationship between the thickness and the width of each member and the scale of each member are different from the actual dimensions and scale. In the drawings, the relationship between dimensions and the scales may be different.

First Embodiment

First, an endoscope system according to a first embodiment will be described. FIG. 1 is a diagram illustrating the schematic structure of an endoscopic portion of the endoscope system according to the first embodiment. As illustrated in FIG. 1, an endoscope 1 according to the first embodiment includes an elongated insertion portion 2, an operation unit 3 that is disposed at the proximal end of the insertion portion 2 and is held by the operator of an endoscope apparatus, and a flexible universal code 4 that extends from the side of the operation unit 3. The universal code 4 includes, for example, a light guide cable or an electric cable.

The insertion portion 2 includes a tip portion 5 having a CMOS sensor as an imaging element provided therein, a curved portion 6 that includes a plurality of curved pieces and can be curved, and a long flexible tube portion 7 that is provided at the proximal end of the curved portion 6 and is long and flexible.

A connector portion 8 is provided at the end of the universal code 4. The connector portion 8 is provided with a light guide connector 9 that is connected to a light source device such that it can be disconnected therefrom, an electric contact portion 10 that is connected to a control device in order to transmit an electric signal of an object image which is converted from an optical signal by the CMOS sensor to a control device for signal processing, and an air supply mouthpiece 11 for sending air to a nozzle of the tip portion 5. The light source device includes a white light source or a special light source and supplies light emitted from the white light source or the special light source as illumination light to the endoscope 1 which is connected through the light guide connector 9. The control device supplies power to the imaging element and receives the electric signal which is converted from an optical signal by the imaging element. The control device processes the electric signal of the image captured by the imaging element and displays the image on the connected display unit. In addition, the control device controls, for example, the gain of the imaging element and outputs a driving signal for driving the imaging element.

The operation unit 3 includes a bending knob 12 that bends the curved portion 6 in the vertical direction and the horizontal direction, a treatment tool insertion portion 13 that inserts a treatment tool 16, such as a biopsy forceps or a laser probe, into the body cavity, and a plurality of switches 14 that are used to operate the control device, the light source device, or peripheral devices, such as an air supply means, a water supply means, and a gas supply means. The treatment tool 16 which is inserted from the treatment tool insertion portion 13 gets out of an opening portion 15 provided at the distal end of the insertion portion 2 through a treatment tool channel which is provided in the treatment tool 16. For example, when the treatment tool 16 is a biopsy forceps, for example, biopsy, such as the collection of an affected tissue, is performed by the biopsy forceps.

Figure 2:
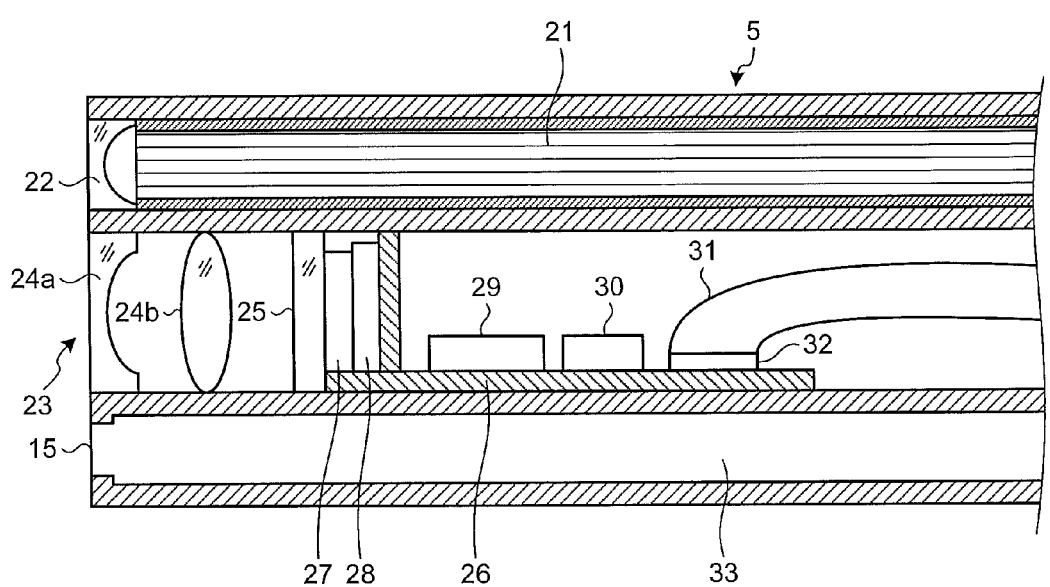
FIG. 2 is a cross-sectional view schematically illustrating the internal structure of a tip portion of the main endoscopic portion illustrated in FIG. 1.

Next, the structure of the tip portion 5 of the insertion portion 2 will be described. FIG. 2 is a cross-sectional view schematically illustrating the internal structure of the tip portion 5 of the endoscope 1 illustrated in FIG. 1. As illustrated in FIG. 2, an illumination lens 22, an observation window 23, the opening portion 15 for a treatment tool which communicates with a treatment tool channel 33, and a nozzle (not illustrated) for supplying air or water are provided at the distal end of the tip portion 5 of the endoscope 1.

White light or special light supplied from the light source device is emitted from the illumination lens 22 through a light guide 21 which is, for example, a glass fiber bundle. A light receiving unit 28 including a plurality of pixels for imaging which are two-dimensionally arranged in a matrix is provided at the imaging position of an optical system including lenses 24a and 24b in the observation window 23. The light receiving unit 28 receives light which is incident through the optical system including the lenses 24a and 24b such that the image of the body cavity is captured. A cover glass 25 is provided on the light receiving surface side of the light receiving unit 28. An on-chip filter 27 in which R, G, and B filters are arranged so as to correspond to the arrangement of the pixels of the light receiving unit 28 is provided between the cover glass 25 and the light receiving unit 28. The light receiving unit 28 is mounted on a circuit board 26 together with, for example, an IC 29 that designates the imaging time of the light receiving unit 28 and reads the image signal obtained by the light receiving unit 28 and a chip condenser 30. An electrode 32 is provided on the circuit board 26. The electrode 32 is connected to an assembled cable 31 that transmits an electric signal to the control device through, for example, an anisotropically-conductive resin film. The assembled cable 31 includes a plurality of signal lines such as a signal line that transmits an image signal, which is an electric signal output from the light receiving unit 28, or a signal line that transmits the control signal from the control device.

Figure 3:
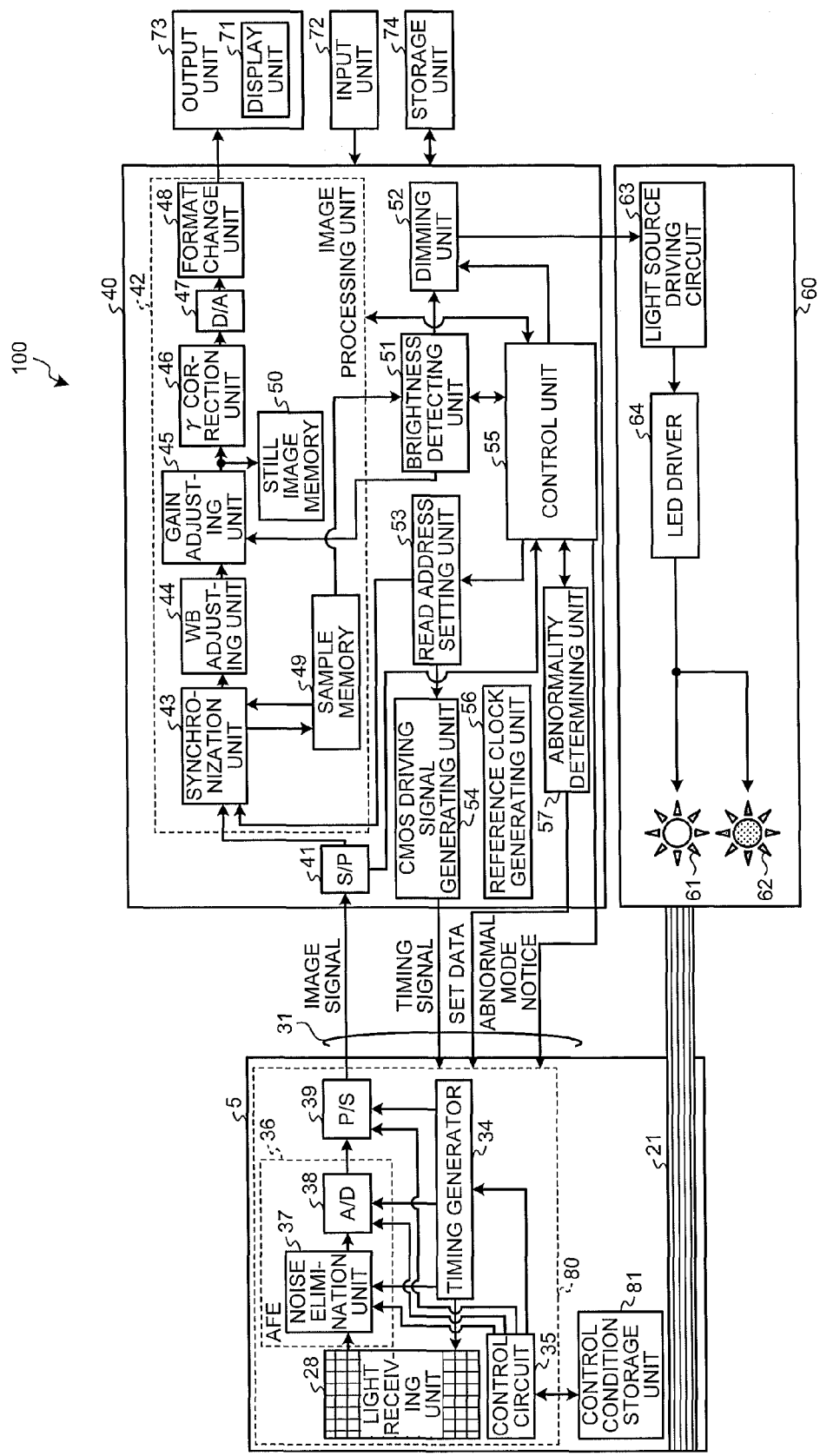
FIG. 3 is a block diagram illustrating the schematic structure of an endoscope system according to the first embodiment.

Next, the structure of the endoscope system according to the first embodiment will be described. FIG. 3 is a block diagram illustrating the structure of the endoscope system according to the first embodiment. As illustrated in FIG. 3, an endoscope system 100 according to the first embodiment includes a control device 40 that is connected to a CMOS imaging element 80 provided in the tip portion 5 through the assembled cable 31 including a plurality of signal lines, a light source device 60 that supplies white light or special light, a display unit 71 that displays an in-vivo image captured by the CMOS imaging element 80, an output unit 73 that outputs information about in-vivo observation, an input unit 72 that inputs various kinds of instruction information required for in-vivo observation, and a storage unit 74 that stores, for example, an in-vivo image.

The CMOS imaging element 80 is provided in the tip portion 5. The CMOS imaging element 80 includes the light receiving unit 28, a timing generator 34, a control circuit 35, an AFE (Analog Front End) unit 36 including a noise elimination unit 37 and an A/D conversion unit 38, and a P/S conversion unit 39 that converts an input digital signal from a parallel signal into a serial signal. The control circuit 35, the timing generator 34, the AFE unit 36, and the P/S conversion unit 39 are provided on a board having the light receiving unit 28 mounted thereon. Therefore, the CMOS imaging element 80 has a one-chip structure in which the light receiving unit 28, the timing generator 34, the control circuit 35, the AFE unit 36, and the P/S conversion unit 39 are mounted on one board.

The light receiving unit 28 outputs an electric signal which is converted from an optical signal as pixel information from an arbitrary pixel designated as a read target among the plurality of pixels for imaging which are two-dimensionally arranged in a matrix. Each pixel information item includes a brightness value.

The timing generator 34 is driven according to a timing signal output from the control device 40 and outputs, as the pixel information, an electric signal which is converted from an optical signal from a pixel which is disposed at the position (address) designated as a read target among the plurality of pixels of the light receiving unit 28 in the reading order set by a read address setting unit 53.

The control circuit 35 controls the imaging process of the light receiving unit 28, the imaging speed of the light receiving unit 28, a process of reading the pixel information from the pixels of the light receiving unit 28, and a process of transmitting the read pixel information, on the basis of set data which is output from the control device 40.

The noise elimination unit 37 eliminates noise in the signal of the pixel information which is output from a predetermined pixel of the light receiving unit 28. The A/D conversion unit 38 converts the signal of the pixel information from which noise has been eliminated from an analog signal into a digital signal and outputs the digital signal to the P/S conversion unit 39. The P/S conversion unit 39 converts a signal including the pixel information which is read from the light receiving unit 28 by the timing generator 34 and the AFE unit 36 from a parallel signal to an image signal of a serial signal constituted in predetermined bit number units and the converted signal is transmitted to the control device 40 through a predetermined signal line of the assembled cable 31. The timing generator 34 and the AFE unit 36 function as a reading unit described in the claims.

A control condition storage unit 81 is further provided in the tip portion 5. The control condition storage unit 81 is connected to the board forming the CMOS imaging element 80. The control condition storage unit 81 stores the control conditions of the pixel information output process of the light receiving unit 28, the pixel information reading process of the timing generator 34 and the AFE unit 36, and the conversion process of the P/S conversion unit 39, the control conditions being for an abnormality occurrence.

When receiving an abnormal mode notification signal for causing execution of control upon the abnormality occurrence, the abnormal mode notification signal being output by an abnormality determining unit 57 of the control device 40, which will be described below, the control circuit 35 directly controls the pixel information output process of the light receiving unit 28, the pixel information reading process of the timing generator 34 and the AFE unit 36, and the conversion process of the P/S conversion unit 39. When receiving the abnormal mode notification signal which is output from the abnormality determining unit 57, the control circuit 35 controls the pixel information output process of the light receiving unit 28, the pixel information reading process of the timing generator 34 and the AFE unit 36, and the conversion process of the P/S conversion unit 39 on the basis of the control conditions stored in the control condition storage unit 81. The control circuit 35 functions as an imaging-side control unit described in the claims.

The control device 40 processes the image signal, directs the display unit 71 to display an in-vivo image, and controls each unit of the endoscope system 100. The control device 40 includes an S/P conversion unit 41, an image processing unit 42, a brightness detecting unit 51, a dimming unit 52, the read address setting unit 53, a CMOS driving signal generating unit 54, a control unit 55, a reference clock generating unit 56, and the abnormality determining unit 57.

The S/P conversion unit 41 converts an image signal, which is a digital signal transmitted from a predetermined signal line of the assembled cable 31, from a serial signal into a parallel signal and outputs the parallel signal to the image processing unit 42.

The image processing unit 42 generates an in-vivo image, which will be displayed on the display unit 71 on the basis of the address of the pixel of the light receiving unit 28 read by the timing generator 34 and the AFE unit 36, from the parallel image signal output from the S/P conversion unit 41, that is, the pixel information of the pixel read by the timing generator 34 and the AFE unit 36.

The image processing unit 42 includes a synchronization unit 43, a WB adjusting unit 44, a gain adjusting unit 45, a γ correction unit 46, a D/A conversion unit 47, a format change unit 48, a sample memory 49, and a still image memory 50.

The synchronization unit 43 inputs the input image signals of R, G, and B pixels to memories (not illustrated) which are provided for each pixel, stores each memory value so as to correspond to the addresses of the pixels of the light receiving unit 28 read by the timing generator 34 and the AFE unit 36 while sequentially updating the memory values with each image signal, and synchronizes the image signals of three memories as R, G, and B image signals. The synchronized R, G, and B image signals are sequentially output to the WB adjusting unit 44. In addition, some of the synchronized R, G, and B image signals are also output to the sample memory 49 for image analysis, such as brightness detection, and are then stored therein.

The WB adjusting unit 44 adjusts the white balance of the R, G, and B image signals. The gain adjusting unit 45 adjusts the gain of the R, G, and B image signals. The γ correction unit 46 performs grayscale conversion on the R, G, and B image signals so as to correspond to the display unit 71.

The D/A conversion unit 47 converts the grayscale-converted R, G, and B image signal from digital signals into analog signals. The format change unit 48 changes the format of the image signal converted into the analog signal to a hi-vision format and outputs the signal to the display unit 71. As a result, one in-vivo image is displayed on the display unit 71. Some of the R, G, and B image signals whose gain has been adjusted by the gain adjusting unit 45 are stored as an image signal for still image display, an image signal for enlarged image display, and an image signal for emphasized image display in the still image memory 50.

The brightness detecting unit 51 detects a brightness level corresponding to each pixel from the R, G, and B image signals stored in the sample memory 49 and stores the detected brightness level in a memory which is provided in the brightness detecting unit 51. In addition, the brightness detecting unit 51 calculates a gain adjustment value and the amount of light emitted, on the basis of the detected brightness level. The calculated gain adjustment value is output to the gain adjusting unit 45 and the calculated amount of light emitted is output to the dimming unit 52. The detection result obtained by the brightness detecting unit 51 is also output to the control unit 55.

The dimming unit 52 sets the amount of current supplied to each light source and the driving conditions of a dimming filter on the basis of the amount of light emitted which is output from the brightness detecting unit 51 under the control of the control unit 55, and outputs a light source synchronous signal including the set conditions to the light source device 60. The dimming unit 52 sets the kind of light emitted from the light source device 60, the amount of light emitted from the light source device 60, and a light emission time.

The read address setting unit 53 can arbitrarily set the read target pixels of the light receiving unit 28 and the order in which the pixels are read. That is, the read address setting unit 53 can arbitrarily set the addresses of the pixels of the light receiving unit 28 which are read by the timing generator 34 and the AFE unit 36. In addition, the read address setting unit 53 outputs the set addresses of the read target pixels to the synchronization unit 43.

The CMOS driving signal generating unit 54 generates a driving timing signal for driving the light receiving unit 28 and a CMOS sensor peripheral circuit and outputs the generated driving timing signal to the timing generator 34 through a predetermined signal line of the assembled cable 31. The timing signal includes the address of the read target pixel. Therefore, the read address setting unit 53 outputs an instruction signal for instructing a reading process for the set read target pixel to the timing generator 34 through the CMOS driving signal generating unit 54.

The control unit 55 includes, for example, a CPU, reads various programs stored in a memory (not illustrated) and performs various processes in the program, thereby controlling the driving of each unit and the input and output of information to and from each unit and processing various kinds of information between the units. The control device 40 outputs set data for imaging control to the control circuit 35 provided in the tip portion 5 through a predetermined signal line of the assembled cable 31. The set data includes, for example, the imaging speed of the light receiving unit 28, instruction information for instructing the reading speed of pixel information from an arbitrary pixel of the light receiving unit 28, and transmission control information of the read pixel information. The control unit 55 changes the read target pixel and the reading order on the basis of the settings of the read address setting unit 53.

The reference clock generating unit 56 generates a reference clock signal, which is a standard for the operation of each unit of the endoscope system 100, and supplies the generated reference clock signal to each unit of the endoscope system 100.

The light source device 60 performs a light emission process under the control of the control unit 55. The light source device 60 includes a white light source 61 which is, for example, an LED and emits white illumination light, a special light source 62 that emits, as special light, any one of R, G, and B light components which are in a wavelength bandwidth different from that of the white illumination light and whose bandwidth is narrowed by a narrow bandpass filter, a light source driving circuit 63 that controls the amount of current supplied to the white light source 61 or the special light source 62 or the driving of the dimming filter on the basis of the light source synchronous signal transmitted from the dimming unit 52, and an LED driver 64 that supplies a predetermined amount of current to the white light source 61 or the special light source 62 under the control of the light source driving circuit 63. Light emitted from the white light source 61 or the special light source 62 is supplied to the insertion portion 2 through the light guide 21 and is then emitted from the distal end of the tip portion 5 to the outside.

The abnormality determining unit 57 determines whether there is an abnormality in the pixel information which has been read by the timing generator 34 and the AFE unit 36, converted by the P/S conversion unit 39, and then transmitted. When it is determined that there is an abnormality in the pixel information which has been read by the timing generator 34 and the AFE unit 36, converted by the P/S conversion unit 39, and then transmitted, the abnormality determining unit 57 outputs, to the control circuit 35, an abnormal mode notification signal for casing the control circuit 35 of the CMOS imaging element 80 provided in the tip portion 5 to execute control for the occurrence of the abnormality. The abnormality determining unit 57 determines whether there is an abnormality in the pixel information which has been read by the timing generator 34 and the AFE unit 36, converted by the P/S conversion unit 39, and then transmitted, on the basis of whether the serial signal transmitted from a predetermined signal line of the assembled cable 31 to the S/P conversion unit 41 is constituted in predetermined bit number units.

In the endoscope system 100 according to the first embodiment, when the abnormality determining unit 57 determines that there is an abnormality in the pixel information which has been read by the timing generator 34 and the AFE unit 36, converted by the P/S conversion unit 39, and then transmitted, the control device 40 only outputs, to the control circuit 35, the abnormal mode notification signal for causing the control circuit 35 of the CMOS imaging element 80 provided in the tip portion 5 to execute the control for the occurrence of the abnormality. Then, the control circuit 35 of the tip portion 5 which has received the abnormal mode notification signal, not the control device 40, directly controls the pixel information output process of the light receiving unit 28, the pixel information reading process of the timing generator 34 and the AFE unit 36, and the conversion process of the P/S conversion unit 39.

Figure 4:
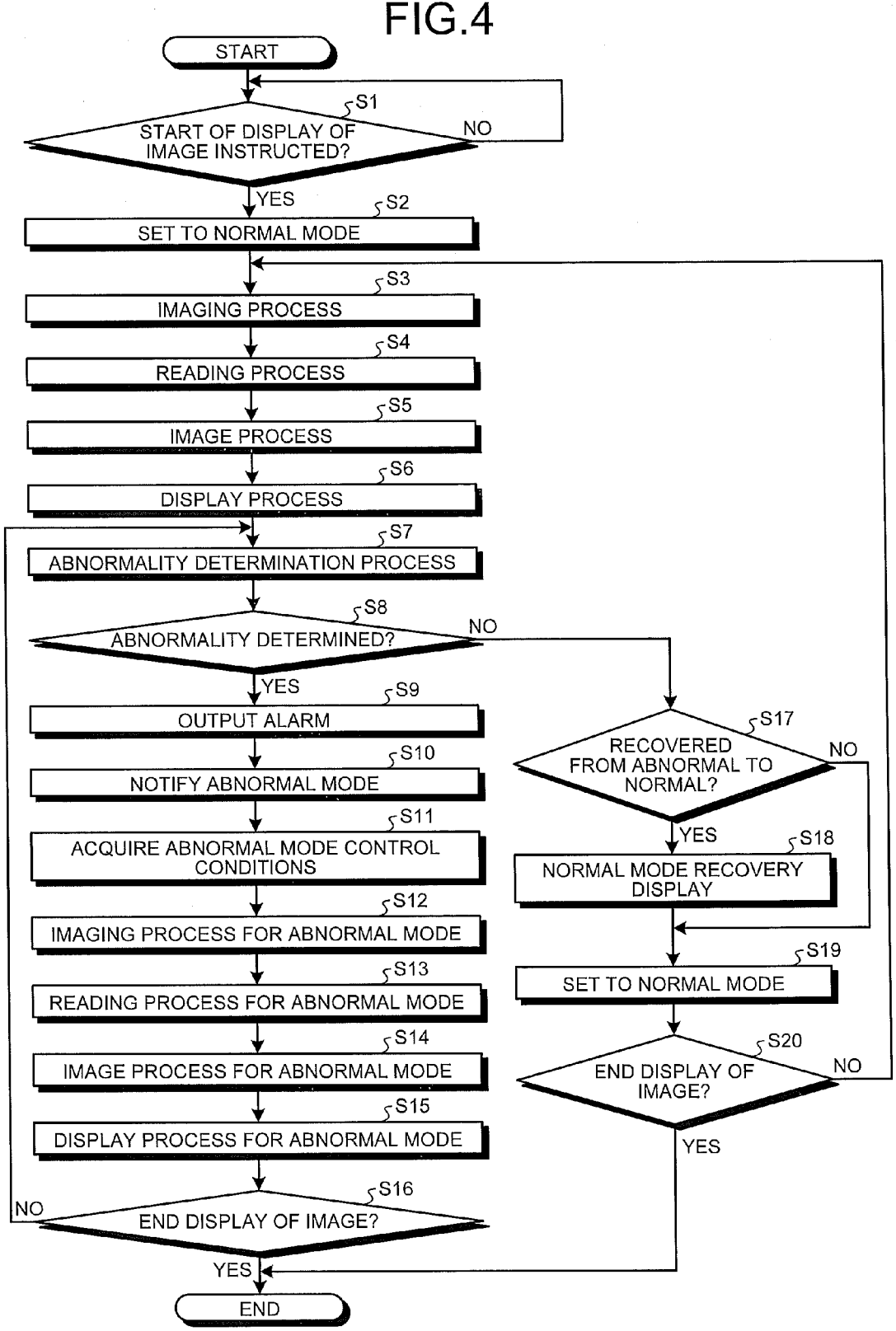
FIG. 4 is a flowchart illustrating the procedure of an in-vivo image display process of the endoscope system illustrated in FIG. 3.

Next, the in-vivo image display process of the endoscope system 100 illustrated in FIG. 3 will be described. FIG. 4 is a flowchart illustrating the procedure of the in-vivo image display process of the endoscope system 100 illustrated in FIG. 3.

As illustrated in the flowchart of FIG. 4, first, the control unit 55 of the control device 40 determines whether there is an instruction to start the display of the in-vivo image on the basis of the instruction information input from, for example, the input unit 72 (Step S1). The control unit 55 repeatedly performs the determining process of Step S1 until it is determined that there is an instruction to start the display of the in-vivo image.

When it is determined that there is an instruction to start the display of the in-vivo image (Step S1: Yes), first, the control unit 55 sets the operation mode to the normal mode (Step S2). In the normal mode, for example, the pixel information of all pixels in a sensor region Si of the light receiving unit 28 is read at a standard frame rate. Therefore, the read address setting unit 53 sets all pixels of the light receiving unit 28 as the read target pixels under the control of the control unit 55. In the tip portion 5, the light receiving unit 28 performs an imaging process at the time when the light source device 60 emits light (Step S3). Then, the timing generator 34 and the AFE unit 36 perform a reading process of reading the pixel information from all pixels of the light receiving unit 28 on the basis of a predetermined timing signal (Step S4). The P/S conversion unit 39 converts a signal including the read pixel information into a serial signal and outputs the serial signal to the assembled cable 31. The serial signal which is transmitted to the control device 40 by the assembled cable 31 is converted into a parallel signal by the S/P conversion unit 41 and is then output to the image processing unit 42. The image processing unit 42 performs an image process of processing the image signals obtained by all pixels of the light receiving unit 28 to generate one high-resolution in-vivo image (Step S5). The display unit 71 displays the image generated by the image processing unit 42 (Step S6).

The abnormality determining unit 57 performs an abnormality determination process of determining whether there is an abnormality in the pixel information which has been read by the timing generator 34 and the AFE unit 36, converted by the P/S conversion unit 39, and then transmitted (Step S7) and outputs the determination result to the control unit 55. Specifically, the abnormality determining unit 57, in the S/P conversion unit 41, counts how many times the image signal of the serial signal having a bit number less than a predetermined number of bits has been input from the assembled cable 31, and if a certain count has been reached, determines that there is an abnormality in the pixel information which has been read by the timing generator 34 and the AFE unit 36, converted by the P/S conversion unit 39, and thereafter transmitted. The control unit 55 determines whether the abnormality determining unit 57 has determined in the abnormality determination process that there is an abnormality in the pixel information which had been read and output by the timing generator 34, the AFE unit 36, and the P/S conversion unit 39 (Step S8).

When the abnormality determining unit 57 determines that there is no abnormality in the pixel information which has been read by the timing generator 34 and the AFE unit 36, converted by the P/S conversion unit 39 and then transmitted in the abnormality determination process (Step S8: No), the control unit 55 proceeds to Step S17, which will be described below.

When the abnormality determining unit 57 determines that there is an abnormality in the pixel information which has been read by the timing generator 34 and the AFE unit 36, converted by the P/S conversion unit 39 and then transmitted in the abnormality determination process (Step S8: Yes), the control unit 55 directs the output unit 73 to output an alarm indicating that there is an abnormality in the pixel information which has been read by the timing generator 34 and the AFE unit 36, converted by the P/S conversion unit 39 and then transmitted (Step S9). Then, the abnormality determining unit 57 outputs via the control unit 55 the abnormal mode notification signal for causing the control circuit 35 on the board of the tip portion 5 to execute the control for the abnormality occurrence (Step S10).

The control circuit 35 receives the abnormal mode notification signal output from the abnormality determining unit 57 and acquires, from the control condition storage unit 81, the control conditions of the light receiving unit 28, the timing generator 34, the AFE unit 36, and the P/S conversion unit 39 for the abnormality occurrence (Step S11). The control conditions for the abnormality occurrence are set such that the operation load of the CMOS imaging element 80 is less than that in the normal mode.

Then, in the tip portion 5, the light receiving unit 28 performs an imaging process for the abnormal mode on the basis of the control conditions acquired by the control circuit 35 under the control of the control circuit 35 (Step S12), and the timing generator 34 and the AFE unit 36 perform a reading process for the abnormal mode which reads the pixel information from a predetermined pixel of the light receiving unit 28 (Step S13). A signal including the read pixel information is converted into a serial signal by the P/S conversion unit 39 and is then output to the assembled cable 31. In this case, the imaging process for the abnormal mode and the reading process for the abnormal mode are performed while the control signal from the control device 40 has priority over the control signal from the control circuit 35. The image processing unit 42 performs an image process of processing the signal including the pixel information which has been read by the reading process for the abnormal mode and then converted into a parallel signal by the S/P conversion unit 41 to generate one in-vivo image (Step S14). In this case, the control unit 55 acquires the image signal in the control device 40 in correspondence with the reading process for the abnormal mode and changes the image generating process of the image processing unit 42 from processing conditions corresponding to the normal mode to processing conditions corresponding to the abnormal mode. The display unit 71 displays the image generated by the image processing unit 42 (Step S15).

Then, the control unit 55 determines whether there is an instruction to end the display of the image on the basis of instruction information input from, for example, the input unit 72 (Step S16). When it is determined that there is an instruction to end the display of the image (Step S16: Yes), the control unit 55 ends the image display process. On the other hand, when it is determined that there is no instruction to end the display of the image (Step S16: No), the control unit 55 returns to Step S7. Then, the abnormality determining unit 57 performs the abnormality determination process. The control unit 55 determines whether there is an abnormality in the pixel information in the abnormality determination process (Step S8).

When the abnormality determining unit 57 determines that there is no abnormality in the pixel information in the abnormality determination process (Step S8: No), the control unit 55 determines whether the pixel information has recovered from the abnormal state to the normal state in the current abnormality determination process (Step S17). When it is determined that the pixel information has recovered from the abnormal state to the normal state in the current abnormality determination process (Step S17: Yes), the control unit 55 displays information indicating that the operation mode has recovered to the normal mode on the display unit 71 (Step S18).

When the normal mode recovery display process (Step S18) ends, or when the normal state is maintained and it is determined in the current abnormality determination process that the pixel information has not recovered from the abnormal state to the normal state (Step S17: No), the control unit 55 sets the operation mode to the normal mode (Step S19). Then, the control unit 55 determines whether there is an instruction to end the display of the image on the basis of instruction information input from, for example, the input unit 72 (Step S20). When it is determined that there is an instruction to end the display of the image (Step S20: Yes), the control unit 55 ends the image display process. On the other hand, it is determined that there is an instruction to end the display of the image (Step S20: No), the control unit 55 returns to Step S3. In the normal mode, the imaging process (Step S3), the reading process of the timing generator 34 and the AFE unit 36 for all pixels (Step S4), the image process of the image processing unit 42 (Step S5), and the display process of the display unit 71 (Step S6) are performed.

Next, the control process of the control circuit 35 when an abnormality occurs will be described. When receiving the abnormal mode notification signal, as the reading process for the abnormal mode, the control circuit 35 sets only some pixels which are extracted from all pixels of the light receiving unit 28 at predetermined intervals, not all pixels of the light receiving unit 28, as the read target pixels of the light receiving unit 28 such that the operation load of the CMOS imaging element 80 is less than that in the normal mode.

Figure 5:
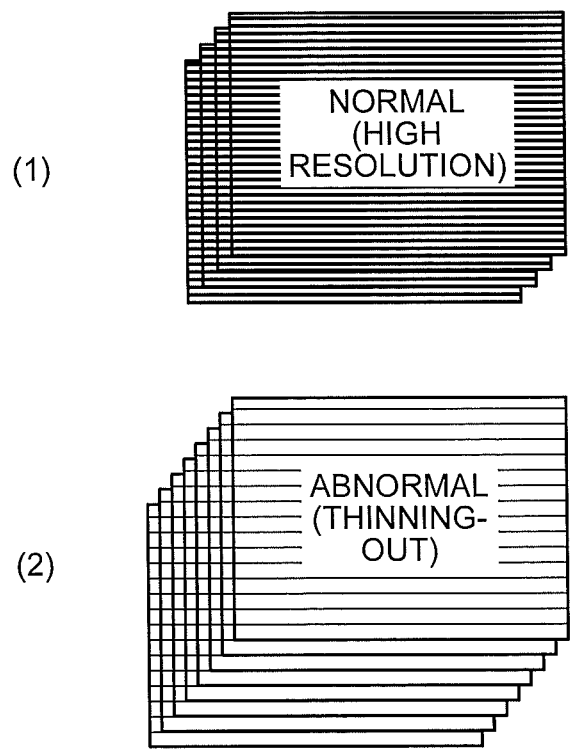
FIG. 5 is a diagram illustrating a pixel of a light receiving unit which is set as a read target.

In the normal mode, as illustrated in (1) of FIG. 5, the read address setting unit 53 sets all pixels of the light receiving unit 28 as read targets under the control of the control unit 55 such that, for example, a high-resolution image with hundreds of thousands of pixel levels is generated.

In contrast, in the abnormal mode, as illustrated in (2) of FIG. 5, the control circuit 35 sets, as the read target pixels, pixels other than the pixels which are thinned out from all pixels of the light receiving unit 28 at predetermined intervals. The thinned image which is generated by the image processing unit 42 on the basis of the pixel information of the thinned pixels has, for example, about a hundred thousand of pixel levels and can be sufficiently used for observation.

Figure 6:
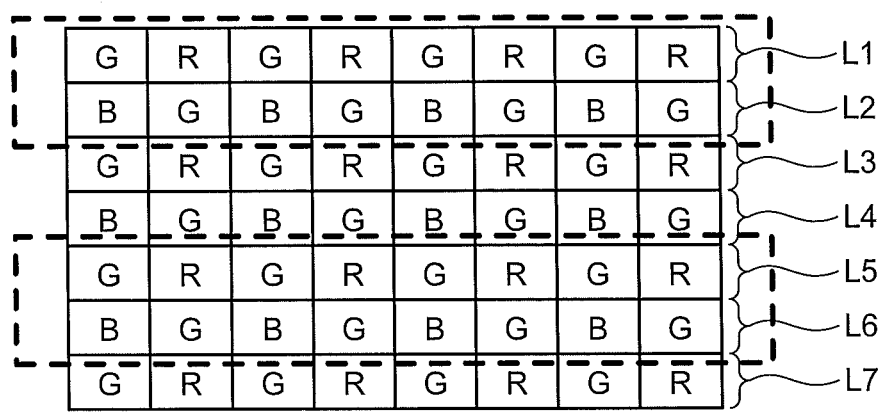
FIG. 6 is a diagram illustrating a reading process in an abnormal mode illustrated in FIG. 4.
Figure 7:
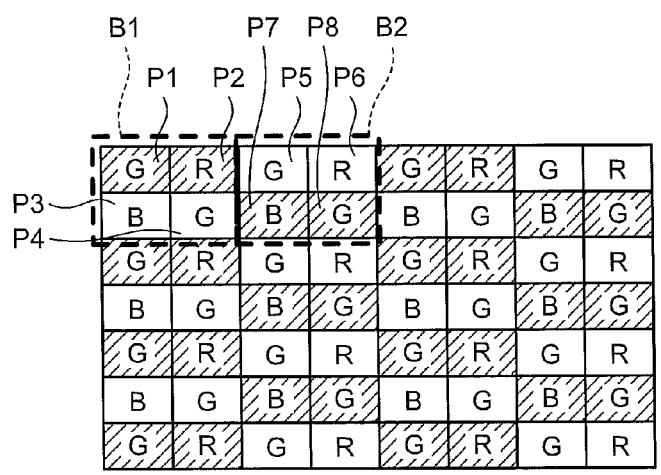
FIG. 7 is a diagram illustrating another example of the reading process in the abnormal mode illustrated in FIG. 4.

As the reading process for the abnormal mode, as illustrated in FIG. 6, the control circuit 35 sets pixels in lines L1 and L2 and lines L5 and L6 among lines L1 to L7 as the read target pixels such that the pixel information is read for every two lines. In addition, the control circuit 35 may be set so as to alternately read the pixel information from two pixels R and G or two pixels G and B. Specifically, as illustrated in FIG. 7, for R, G, G, and B pixels forming a block B1, two R and G pixels P1 and P2 are set as the read target pixels and the remaining pixels P3 and P4 are not set as the read target pixels. For a block B2 adjacent to the block B1, two B and G pixels P7 and P8 are set as the read target pixels and the remaining pixels P5 and P6 are not set as the read target pixels. The control circuit 35 may set the read target pixels such that the pixel information is read from every two lines in the vertical direction. Alternatively, all pixels may be divided into blocks each including a predetermined number of pixels equal to or more than four pixels and the control circuit 35 may set the read target pixels in a block unit.

As such, in the first embodiment, when there is an abnormality in the pixel information which has been read by the timing generator 34 and the AFE unit 36, converted by the P/S conversion unit 39, and then transmitted, the timing generator 34, the AFE unit 36, and the P/S conversion unit 39 are controlled by the control circuit 35 such that the pixel information is read from some pixels, not all pixels of the light receiving unit 28. In other words, when receiving the abnormal mode notification signal output from the abnormality determining unit 57, the control circuit 35 controls the pixel information reading process of the timing generator 34 and the AFE unit 36 such that the amount of signals processed by the AFE unit 36 and the P/S conversion unit 39 per unit time is less than the amount of signals processed per unit time in the normal mode. That is, in the first embodiment, when there is an abnormality, the control circuit 35 eases the operation conditions of each circuit of the CMOS imaging element 80, operates each circuit at a low speed, and reduces the amount of signals transmitted to the assembled cable 31 per unit time.

Therefore, in the first embodiment, when an abnormality occurs, the operation load of the CMOS imaging element 80 is less than that in the normal mode. Therefore, it is possible to reduce the amount of heat generated from the chip, as compared to a case in which the pixel information is read from all pixels, and thus stabilize the operation of each circuit of the CMOS imaging element 80. Therefore, in the first embodiment, it is possible to prevent an increase in the temperature of the chip and reliably prevent the damage of the chip. In the first embodiment, it is possible to appropriately transmit the pixel information while reducing the occurrence of a signal abnormality due to the unstable operation or contact failure of the CMOS imaging element caused by heat. Therefore, according to the first embodiment, it is possible to stably acquire the captured image.

In the first embodiment, when an abnormality occurs, the control circuit 35 of the CMOS imaging element 80, not the control device 40, controls the light receiving unit 28, the timing generator 34, the AFE unit 36, and the P/S conversion unit 39. Therefore, when an abnormality occurs, the control device 40 does not need to transmit the control signal to each of the light receiving unit 28, the timing generator 34, the AFE unit 36, and the P/S conversion unit 39, but outputs only the abnormal mode notification signal to the control circuit 35 of the tip portion 5. As a result, in the first embodiment, the control corresponding to the occurrence of an abnormality is performed, it is possible to reduce the amount of signals transmitted from the control device 40 to the tip portion 5 and effectively respond to the occurrence of an abnormality.

The process for reducing the operation load of the CMOS imaging element 80 as compared to the normal mode is not limited to the process of thinning out the pixels and reading the pixel information from the pixels. For example, the control circuit 35 controls the imaging time of the light receiving unit 28 and the reading speed of the timing generator 34 and the AFE unit 36 such that the frame rate on the occurrence of an abnormality is less than the standard frame rate in the normal mode. After the abnormal mode notification signal is output, the control unit 55 controls the light emission process of the light source device 60 so as to correspond to a low reading speed in the abnormal mode.

Figure 8:
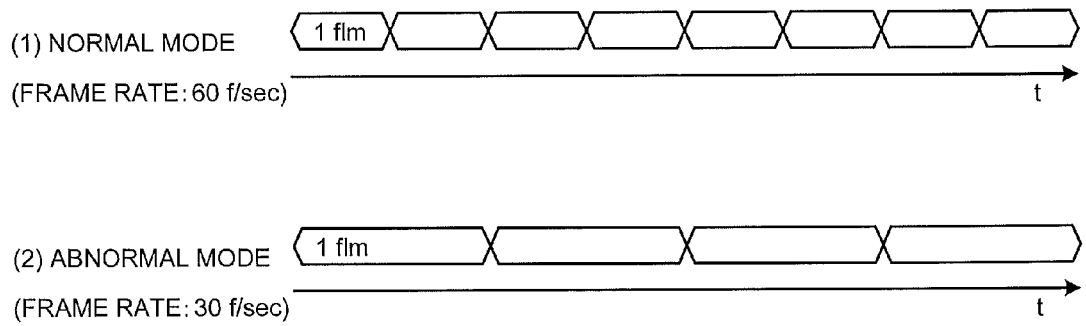
FIG. 8 is a diagram illustrating the reading process illustrated in FIG. 4.

For example, as illustrated in (1) of FIG. 8, if the standard frame rate is 60 f/sec in the normal mode, the control circuit 35 controls the imaging time of the light receiving unit 28 and the reading speed of the timing generator 34 and the AFE unit 36 at 30 f/sec that is half the standard frame rate when an abnormality occurs, as illustrated in (2) of FIG. 8. As a result, when an abnormality occurs, the amount of signals processed by the AFE unit 36 and the P/S conversion unit 39 per unit time is half that in the normal mode. As such, when an abnormality occurs, the operation load of the CMOS imaging element 80 is reduced to be less than that in the normal mode under the control of the control circuit 35. Therefore, the amount of heat generated is reduced as compared to that in the normal mode and each circuit is stabilized.

When an abnormality occurs, the control circuit 35 may control the imaging time of the light receiving unit 28 and the reading speed of the timing generator 34 and the AFE unit 36 such that the frame rate is less than the standard frame rate in the normal mode, and may control the timing generator 34, the AFE unit 36, and the P/S conversion unit 39 such that the pixel information is read from some thinned pixels, not all pixels of the light receiving unit 28.

The control condition storage unit 81 may store a plurality of control conditions by which the number of pixels thinned out in the reading process or the frame rate for the abnormality occurrence are set, according to an extent of the abnormality. The control circuit 35 may select a control condition corresponding to the degree of abnormality which is indicated by the anomalous mode notification signal from the plurality of control conditions stored in the control condition storage unit 81 and control the timing generator 34, the AFE unit 36, and the P/S conversion unit 39.

When the abnormality determining unit 57 determines that there is an abnormality in the pixel information which has been read by the timing generator 34 and the AFE unit 36, converted by the P/S conversion unit 39, and then transmitted, the control unit 55 may control the white light source 61 or the special light source 62 such that the amount of light emitted from the white light source 61 or the special light source 62 is reduced. In this way, the chip temperature of the tip portion 5 is reduced and the processing operations of the light receiving unit 28, the timing generator 34, the AFE unit 36, and the P/S conversion unit 39 are stabilized. In this case, the CMOS imaging element 80 amplifies the image signal and outputs the amplified image signal, and the control device 40 amplifies the image signal and then performs an image process.

When a communication protocol abnormality is detected, the abnormality determining unit 57 may determine that there is an abnormality in the pixel information which has been read by the timing generator 34 and the AFE unit 36, converted by the P/S conversion unit 39 and then transmitted and notify the occurrence of the abnormality to the board of the tip portion 5 provided with the CMOS imaging element 80.

First Modification of First Embodiment

Figure 9:
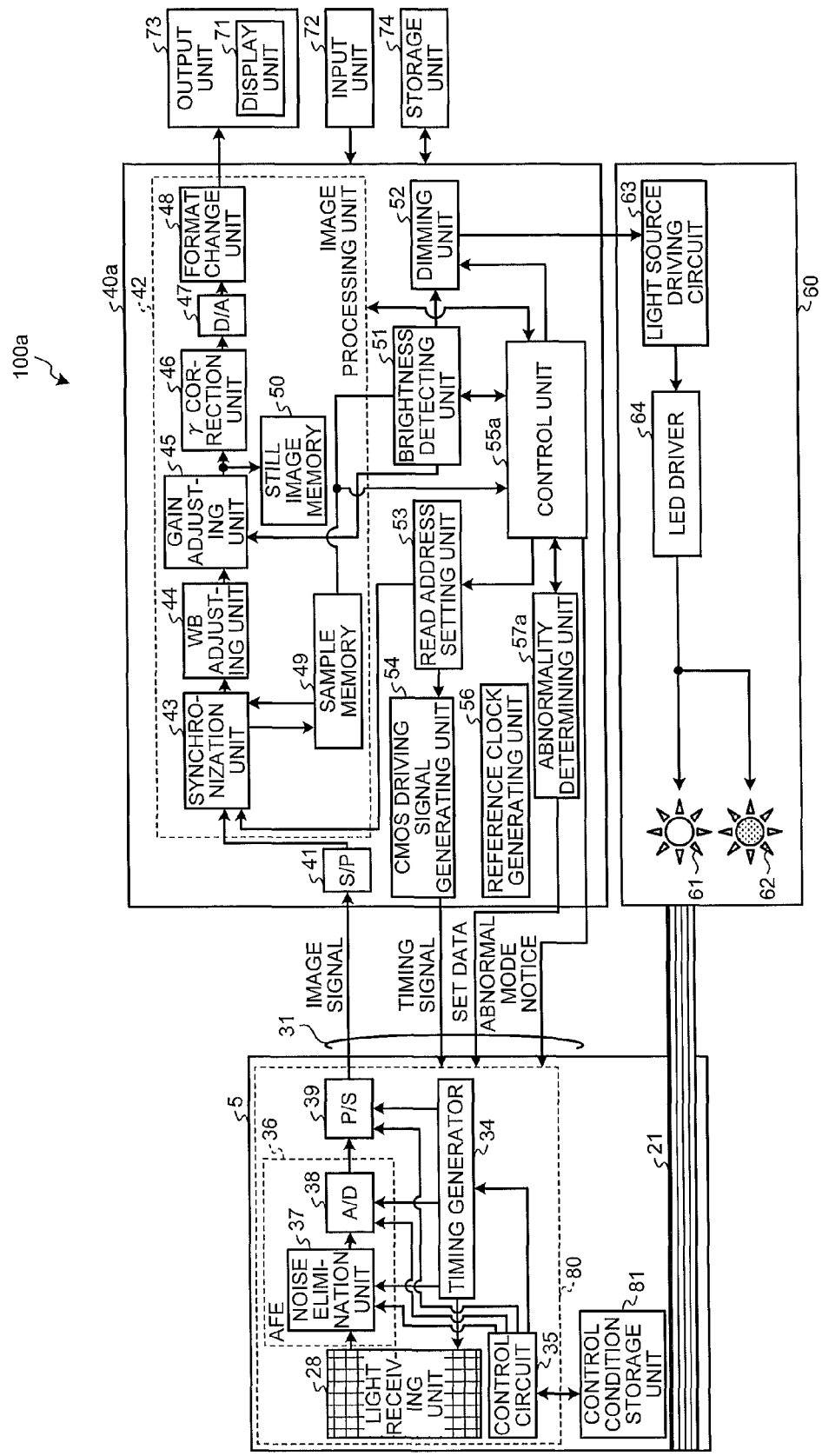
FIG. 9 is a block diagram illustrating the structure of an endoscope system according to a first modification of the first embodiment.

Next, a first modification of the first embodiment will be described. FIG. 9 is a block diagram illustrating the structure of an endoscope system according to the first modification of the first embodiment. As illustrated in FIG. 9, a control device 40a of an endoscope system 100a includes a control unit 55a which has the same function as the control unit 55, instead of the control unit 55 illustrated in FIG. 3.

A light-shielded pixel on which light is not incident is provided in each line in the light receiving unit 28 in order to acquire a reference level during A/D conversion. The control unit 55a directs the timing generator 34 and the AFE unit 36 of the tip portion 5 to read the pixel information of a pixel on which light is incident and the pixel information of the pixel on which light is not incident and outputs the pixel information to the control device 40a. The control unit 55a stores the image signal and the pixel information of the light-shielded pixel in the sample memory 49. In this case, the control unit 55a may store the image signal and the read pixel information of the light-shielded pixel in the sample memory 49 such that the pixel information is separated from the image signal.

The control device 40a includes an abnormality determining unit 57a that determines whether there is an abnormality in the pixel information which has been read by the timing generator 34 and the AFE unit 36 and then output, on the basis of a change in the brightness value of the pixel information of the light-shielded pixel on which light is not incident, which is stored in the sample memory 49.

When the average level of the brightness value of the pixel information of the light-shielded pixel on which light is not incident, which is stored in the sample memory 49, reaches a predetermined value, the abnormality determining unit 57a determines that there is an abnormality in the pixel information which has been read by the timing generator 34 and the AFE unit 36, converted by the P/S conversion unit 39, and then transmitted. In addition, when the difference between the average levels of the brightness values of the pixel information items of adjacent pixels among the light-shielded pixels is monitored and is greater than a predetermined value, the abnormality determining unit 57a may determine that there is an abnormality in the pixel information which has been read by the timing generator 34 and the AFE unit 36 and then output. Each predetermined value, which is a criterion, is set so as to correspond to the amount of noise of the reference level during A/D conversion which increases due to an increase in the temperature of the board.

As in the first modification of the first embodiment, the timing generator 34 and the AFE unit 36 may read the pixel information of the pixel on which no light is incident and it may be determined whether there is an abnormality in the pixel information which has been read by the timing generator 34 and the AFE unit 36, converted by the P/S conversion unit 39, and then transmitted, on the basis of the brightness value of the pixel information of the pixel on which no light is incident.

Second Modification of First Embodiment

Figure 10:
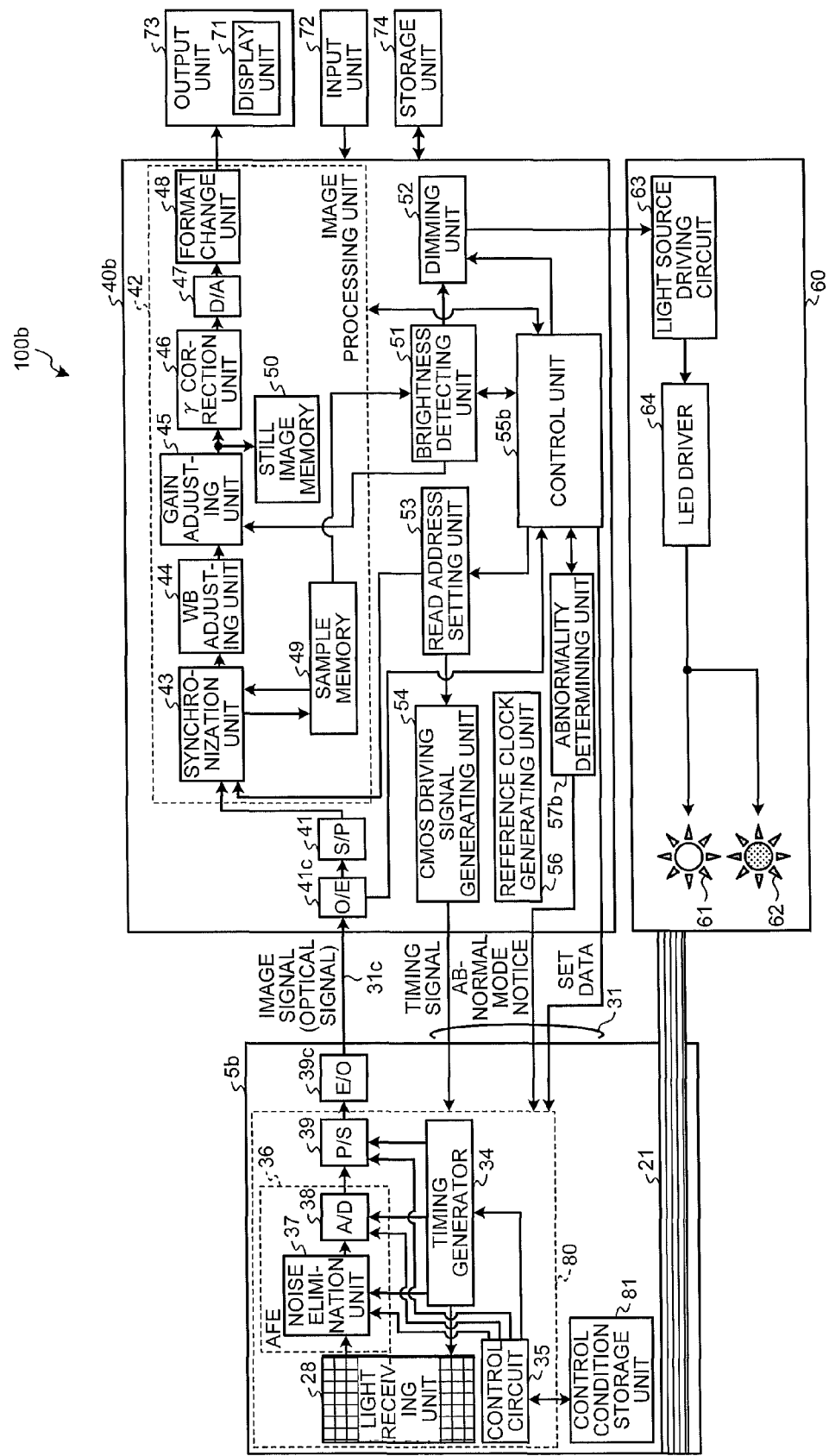
FIG. 10 is a block diagram illustrating the structure of an endoscope system according to a second modification of the first embodiment.

Next, a second modification of the first embodiment will be described. An endoscope system according to the second modification of the first embodiment has a structure in which an image signal, which is an electric signal output from a CMOS imaging element, is converted into an optical signal and the optical signal is transmitted through an optical fiber cable. FIG. 10 is a block diagram illustrating the structure of the endoscope system according to the second modification of the first embodiment.

As illustrated in FIG. 10, in an endoscope system 100b according to the second modification of the first embodiment, a tip portion 5b of an endoscope and a control device 40b are connected to each other by an optical fiber cable 31c, an image signal is converted into an optical signal and the optical signal is transmitted, which makes it possible to transmit a large amount of signals. In this case, the tip portion 5b of the endoscope further includes an E/O conversion unit 39c that converts an electric signal including pixel information output from the CMOS imaging element 80 into an optical signal and outputs the optical signal to the optical fiber cable 31c. The control device 40b may include an O/E conversion unit 41c that converts an optical signal into an electric signal and outputs the converted electric signal to the image processing unit 42 through the S/P conversion unit 41.

The control device 40b includes a control unit 55b that has the same function as the control unit 55, instead of the control unit 55 illustrated in FIG. 3. The control device 40b includes an abnormality determining unit 57b that determines whether there is an abnormality in the pixel information which has been read by the timing generator 34 and the AFE unit 36, converted by the P/S conversion unit 39, and then transmitted, on the basis of a change in the intensity of the optical signal transmitted through the optical fiber cable 31c. When the intensity of the optical signal transmitted through the optical fiber cable 31c is less than a predetermined value, the abnormality determining unit 57b determines that there is an abnormality in the pixel information due to the damage of the optical fiber cable 31c.

As in the second modification of the first embodiment, it may be determined whether there is an abnormality in the pixel information which has been read by the timing generator 34 and the AFE unit 36, converted by the P/S conversion unit 39, and then transmitted, on the basis of a change in the intensity of the optical signal transmitted through the optical fiber cable 31c.

Figure 11:
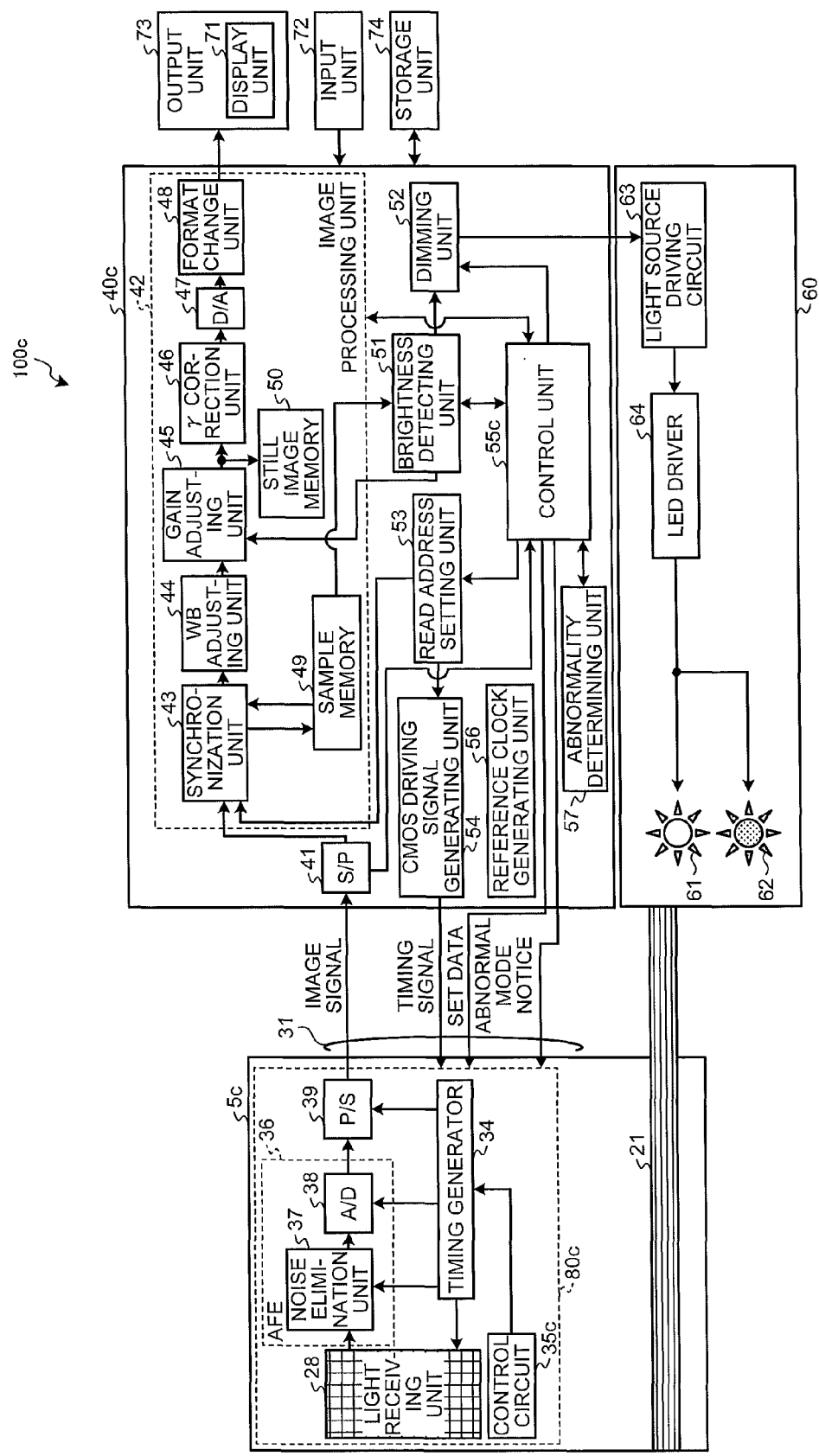
FIG. 11 is a block diagram illustrating another structure of the endoscope system according to the first embodiment.

In the first embodiment, as in an endoscope system 100c illustrated in FIG. 11, a control unit 55c of a control device 40c, not a control circuit 35c, may output anomalous mode setting data for controlling the light receiving unit 28, the timing generator 34, the AFE unit 36, and the P/S conversion unit 39 to a CMOS imaging element 80c of a tip portion 5c, in correspondence with the abnormality determined by the abnormality determining unit 57, thereby controlling each circuit of the CMOS imaging element 80c.

Second Embodiment

Figure 12:
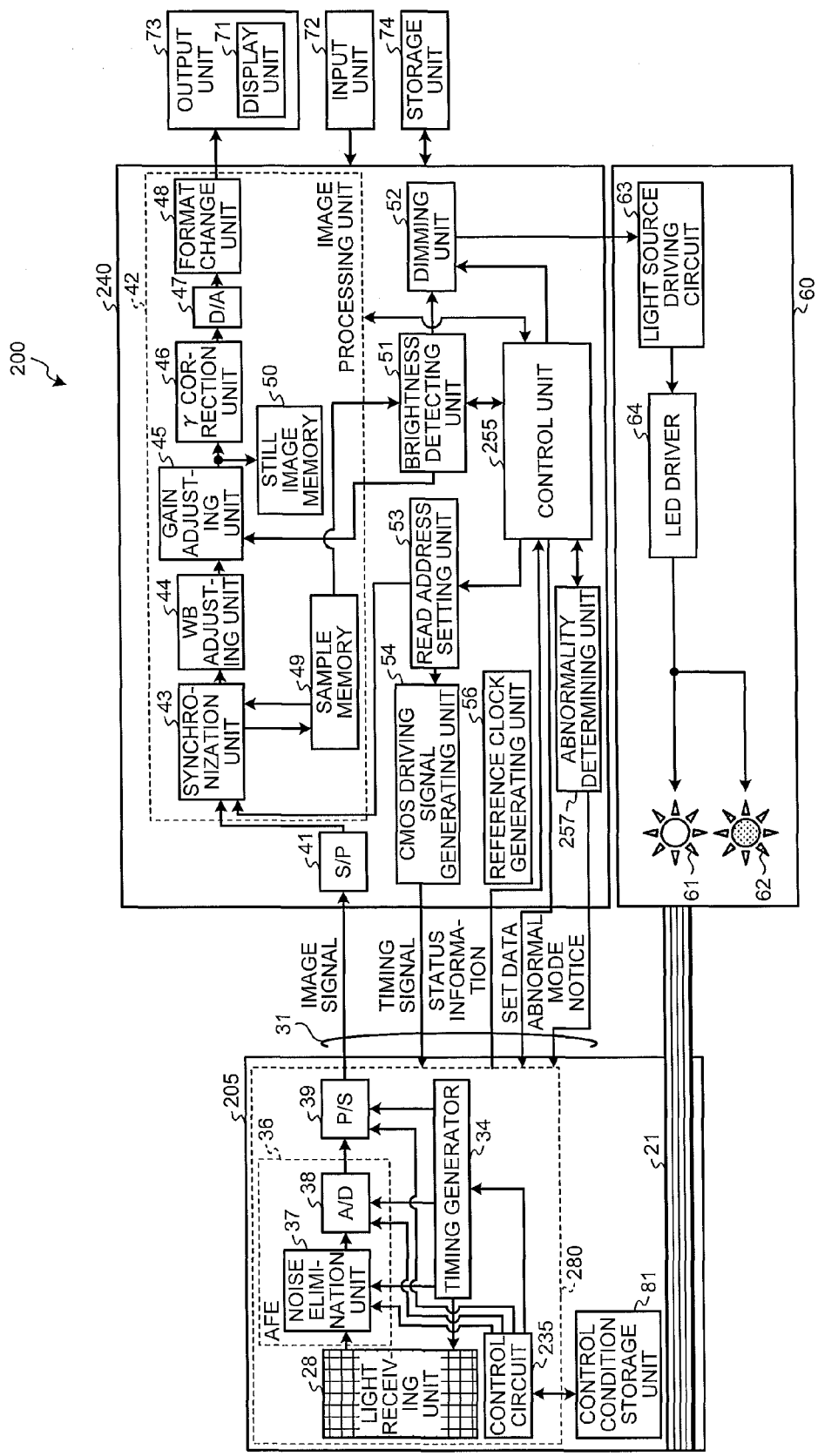
FIG. 12 is a block diagram illustrating the structure of an endoscope system according to a second embodiment.

Next, a second embodiment will be described. FIG. 12 is a block diagram illustrating the structure of an endoscope system according to the second embodiment. As illustrated in FIG. 12, a tip portion 205 of an endoscope system 200 includes a CMOS imaging element 280 including a control circuit 235, instead of the CMOS imaging element 80 illustrated in FIG. 3.

The control circuit 235 has the same function as the control circuit 35 illustrated in FIG. 3, has a function of storing status information including information indicating whether there is an abnormality in a light receiving unit 28, a timing generator 34, an AFE unit 36, and a P/S conversion unit 39, and transmits the status information to a control device 240 when receiving an instruction to transmit the status information from the control device 240.

The control device 240 of the endoscope system 200 includes a control unit 255 that has the same function as the control unit 55 and includes an abnormality determining unit 257, instead of the control unit 55 illustrated in FIG. 3. The abnormality determining unit 257 instructs the control circuit 235 of the tip portion 205 to transmit the status information through the control unit 255 and determines whether there is an abnormality in pixel information which has been read by the timing generator 34 and the AFE unit 36, converted by the P/S conversion unit 39, and then transmitted, on the basis of the status information transmitted from the control circuit 235.

Figure 13:
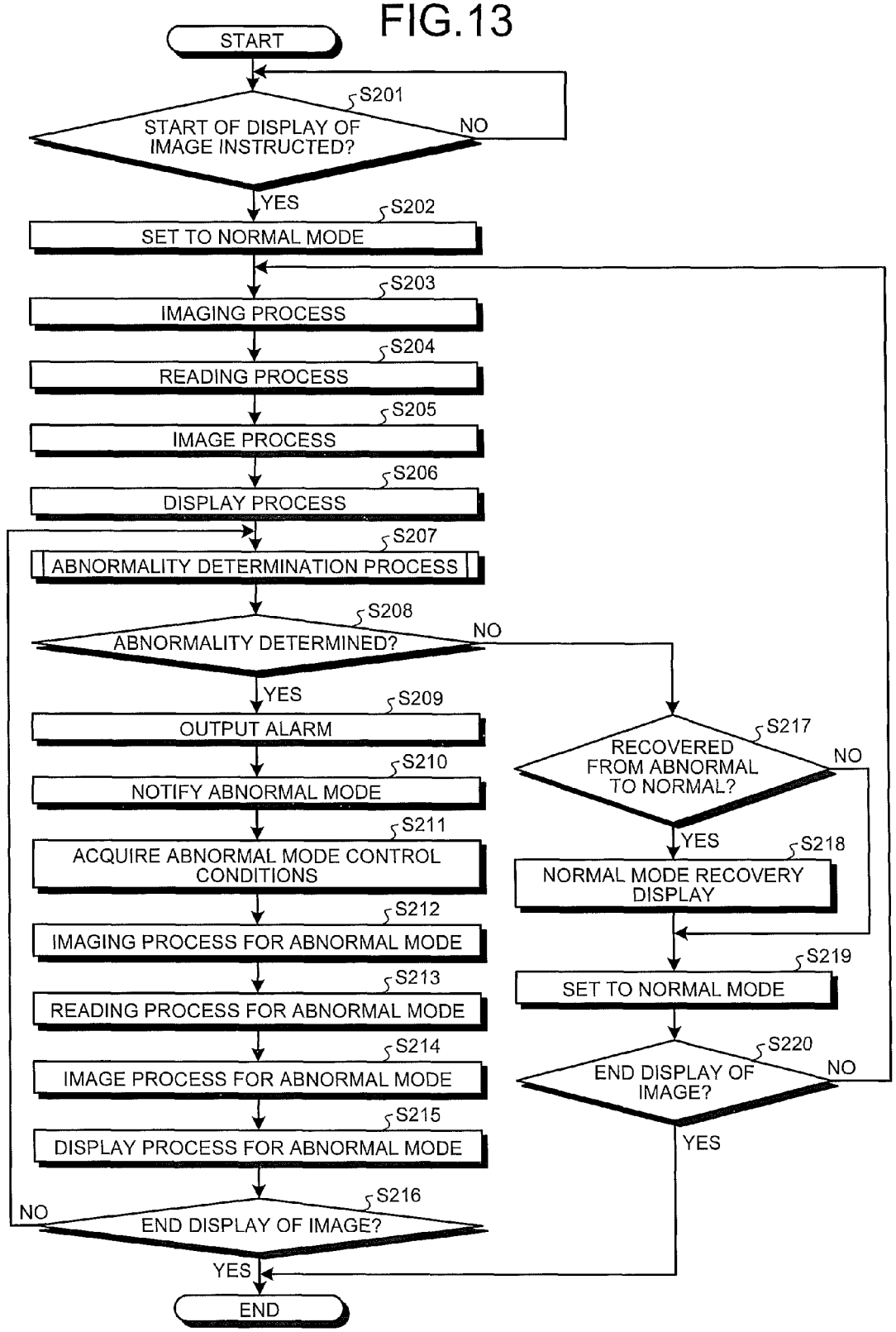
FIG. 13 is a flowchart illustrating the procedure of an in-vivo image display process of the endoscope system illustrated in FIG. 12.

Next, an in-vivo image display process of the endoscope system 200 illustrated in FIG. 12 will be described. FIG. 13 is a flowchart illustrating the procedure of the in-vivo image display process of the endoscope system 200 illustrated in FIG. 12.

As illustrated in the flowchart of FIG. 13, the control unit 255 determines whether there is an instruction to start the display of the in-vivo image, similarly to Step S1 in FIG. 4 (Step S201). The control unit 255 repeatedly performs the determination process in Step S201 until an instruction to start the display of the in-vivo image is input.

When it is determined that there is an instruction to start the display of the in-vivo image (Step S201: Yes), the control unit 255 performs a normal mode setting process (Step S202), an imaging process of the light receiving unit 28 (Step S203), a reading process of the timing generator 34 and the AFE unit 36 for all pixels (Step S204), the image process of an image processing unit 42 for a high-resolution image (Step S205), and a high-resolution image display process of a display unit 71 (Step S206), similarly to Steps S2 to S6 in FIG. 4.

Then, the abnormality determining unit 257 performs an abnormality determination process of determining whether there is an abnormality in the pixel information which has been read by the timing generator 34 and the AFE unit 36, converted by the P/S conversion unit 39, and then transmitted (Step S207) and outputs the determination result to the control unit 255. The control unit 255 determines whether the abnormality determining unit 257 determines that there is an abnormality in the pixel information which has been read by the timing generator 34 and the AFE unit 36, converted by the P/S conversion unit 39, and then transmitted, in the abnormality determination process (Step S208).

When the abnormality determining unit 257 determines that there is an abnormality in the pixel information in the abnormality determination process (Step S208: Yes), the control unit 255 performs the output of an alarm by an output unit 73 (Step S209), an abnormal mode notification process of the control circuit 235 (Step S210), the process of the control circuit 235 acquiring control conditions corresponding to the abnormal mode (Step S211), the imaging process of the light receiving unit 28 in the abnormal mode (Step S212), the reading process of the timing generator 34 and the AFE unit 36 in the abnormal mode (Step S213), the image process of the image processing unit 42 in the abnormal mode (Step S214), the display process of the display unit 71 in the abnormal mode (Step S215), and a process of determining the end of image display (Step S216), similarly to Steps S9 to S16 in FIG. 4.

When the abnormality determining unit 257 determines that there is no abnormality in the pixel information in the abnormality determination process (Step S208: No), the control unit 255 performs a determination process of determining whether the pixel information has recovered from the abnormal state to the normal state in the current abnormality determination process (Step S217) and performs a normal mode recovery display process (Step S218), a normal mode setting process (Step S219), and a determination process of determining the end of image display (Step S220), similarly to Steps S17 to S20 in FIG. 4.

Figure 14:
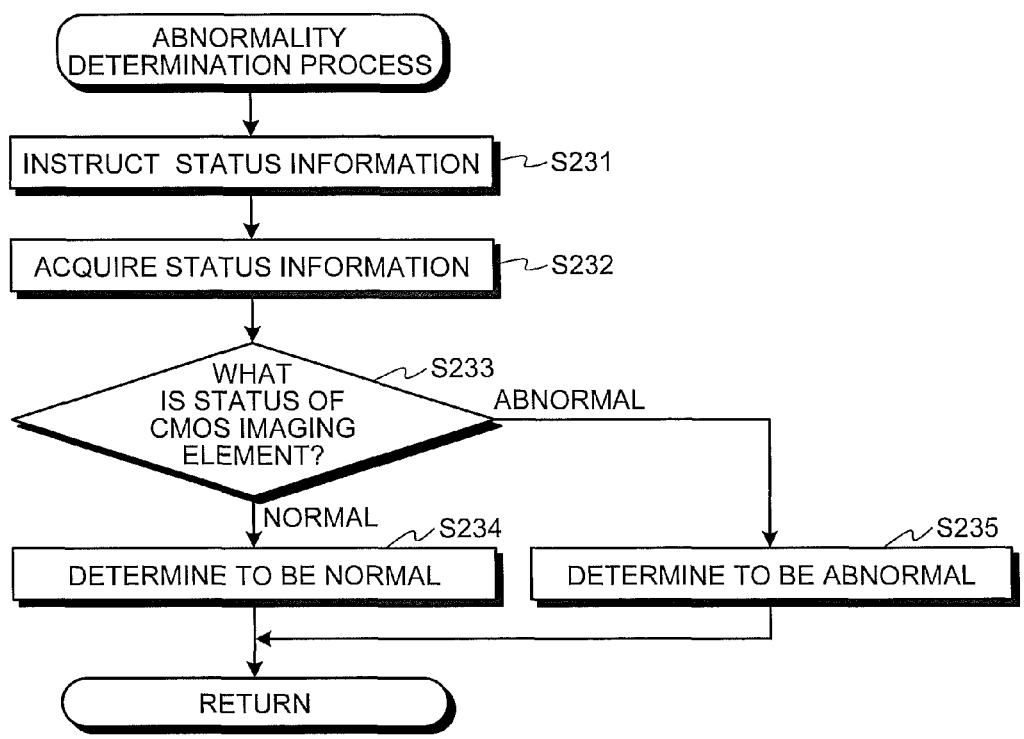
FIG. 14 is a flowchart illustrating the procedure of an abnormality determination process illustrated in FIG. 13.

Next, the abnormality determination process illustrated in FIG. 13 will be described. FIG. 14 is a flowchart illustrating the procedure of the abnormality determination process illustrated in FIG. 13. As illustrated in FIG. 14, the abnormality determining unit 257 instructs the control circuit 235 of the tip portion 205 to transmit the status information through the control unit 255 (Step S231), directs the control circuit 235 to transmit the status information, and acquires the status information (Step S232).

Then, the abnormality determining unit 257 determines whether the acquired status information is normal or abnormal (Step S233). When it is determined that the acquired status information is normal (Step S233: normal) the abnormality determining unit 257 determines that the pixel information which has been read by the timing generator 34 and the AFE unit 36, converted by the P/S conversion unit 39, and then transmitted is normal (Step S234). On the other hand, When it is determined that the acquired status information indicates abnormality (Step S233: abnormal), the abnormality determining unit 257 determines that the pixel information which has been read by the timing generator 34 and the AFE unit 36, converted by the P/S conversion unit 39, and then transmitted is abnormal (Step S235).

As in the second embodiment, the control circuit 235 of the CMOS imaging element 280 in the tip portion 205 may have a function of monitoring the state of each component of the CMOS imaging element 280 and stores the status information, and the abnormality determining unit 257 of the control device 240 may determine whether there is an abnormality in the pixel information which has been read by the timing generator 34 and the AFE unit 36, converted by the P/S conversion unit 39, and then transmitted on the status information transmitted from the tip portion 205.

Third Embodiment

Figure 15:
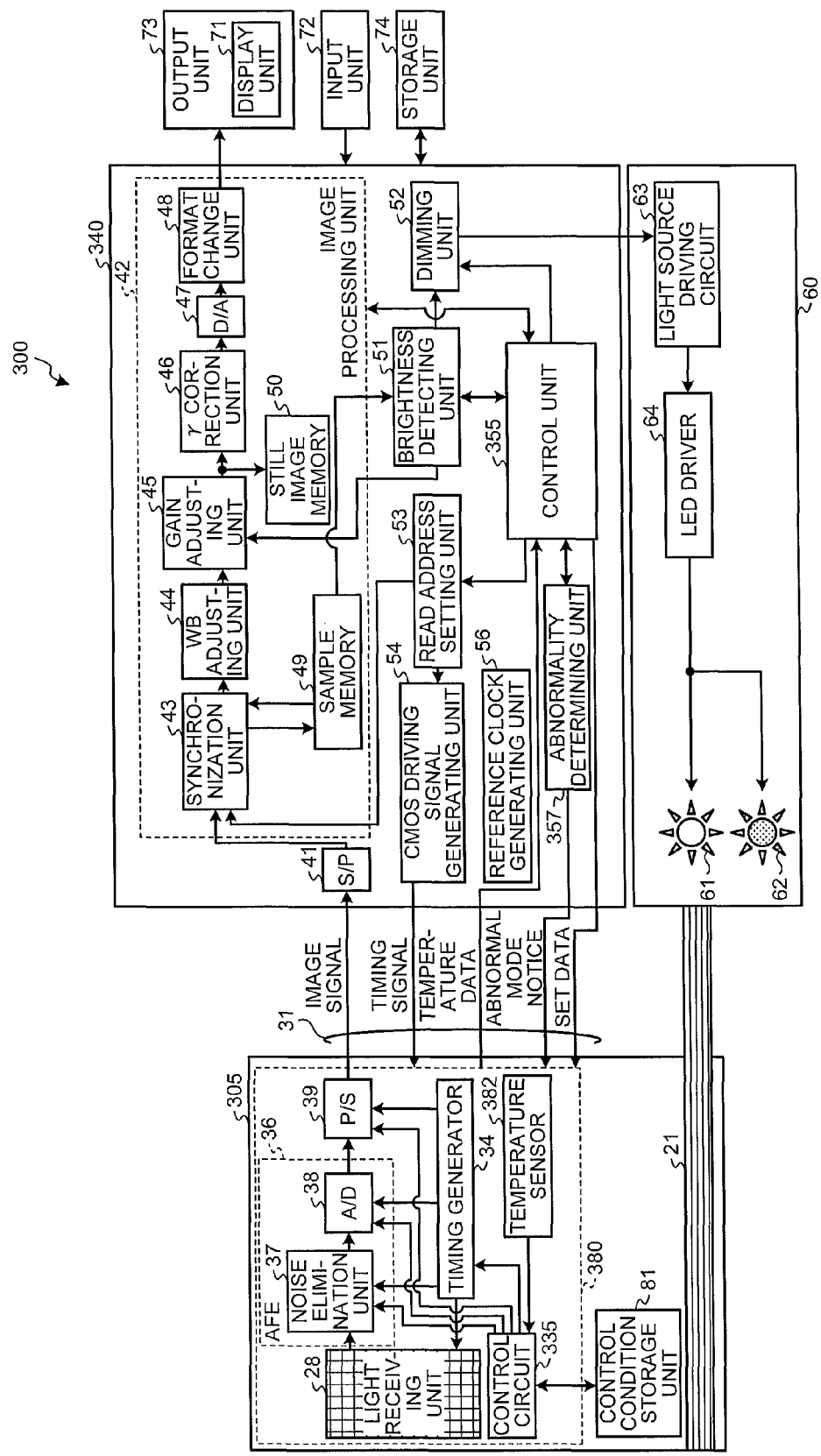
FIG. 15 is a block diagram illustrating the structure of an endoscope system according to a third embodiment.

Next, a third embodiment will be described. FIG. 15 is a block diagram illustrating the structure an endoscope system according to the third embodiment. As illustrated in FIG. 15, a tip portion 305 of an endoscope system 300 includes a CMOS imaging element 380 including a temperature sensor 382 which detects the temperature of a board forming the CMOS imaging element 380 and is provided on the board, instead of the CMOS imaging element 80 illustrated in FIG. 3. The CMOS imaging element 380 includes a control circuit 335 that has the same function as the control circuit 35 and controls the output of the temperature of the board detected by the temperature sensor 382 to a control device 340, instead of the control circuit 35 illustrated in FIG. 3.

The control device 340 includes a control unit 355 which has the same function as the control unit 55 and includes an abnormality determining unit 357, instead of the control unit 55 illustrated in FIG. 3. The abnormality determining unit 357 determines whether there is an abnormality in the pixel information which has been read by a timing generator 34 and an AFE unit 36, converted by a P/S conversion unit 39, and then transmitted, on the basis of the temperature of the board of the CMOS imaging element 380 which is detected by the temperature sensor 382.

Figure 16:
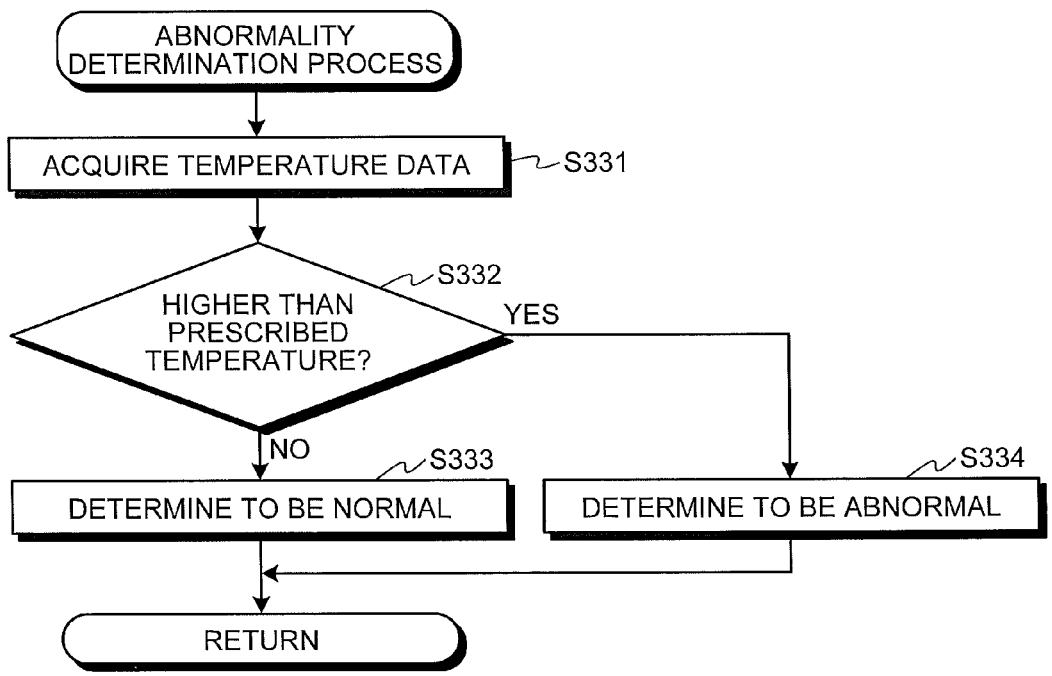
FIG. 16 is a flowchart illustrating the procedure of an abnormality determination process of the endoscope system illustrated in FIG. 15.

Next, an in-vivo image display process of the endoscope system 300 illustrated in FIG. 15 will be described. The endoscope system 300 performs the same process as that illustrated in FIG. 13 to display an in-vivo image. Next, an abnormality determination process of the endoscope system 300 illustrated in FIG. 15 will be described with reference to FIG. 16. FIG. 16 is a flowchart illustrating the procedure of the abnormality determination process of the endoscope system 300 illustrated in FIG. 15.

The control circuit 335 of the tip portion 305 directs the temperature sensor 382 to detect the temperature of the board and directs the control device 340 to output data for the temperature of the board. In this way, as illustrated in the flowchart of FIG. 16, the abnormality determining unit 357 acquires the data for the temperature of the board through the control unit 355 (Step S331). In this case, the control circuit 335 directs the temperature sensor 382 to periodically detect the temperature and outputs temperature data to the control unit 355. Alternatively, when data for an instruction to output the temperature data is transmitted from the abnormality determining unit 357 through the control unit 355, the control circuit 335 directs the temperature sensor 382 to detect the temperature and outputs the temperature data to the control device 340. The temperature detected by the temperature sensor 382 is received by the control circuit 335 and is then stored in an internal register (not illustrated) of the CMOS imaging element 380 or a control condition storage unit 81.

Then, the abnormality determining unit 357 determines whether the temperature of the board indicated by the acquired temperature data is equal to or more than a prescribed temperature (Step S332). The prescribed temperature is set on the basis of a board temperature range in which a light receiving unit 28, the timing generator 34, the AFE unit 36, and the P/S conversion unit 39 can operate normally in the normal mode.

When it is determined that the temperature of the board indicated by the acquired temperature data is less than the prescribed temperature (Step S332: No), the abnormality determining unit 357 determines that the pixel information which has been read by the timing generator 34 and the AFE unit 36, converted by the P/S conversion unit 39, and then transmitted is normal (Step S333). On the other hand, when it is determined that the temperature of the board indicated by the acquired temperature data is equal to or more than the prescribed temperature (Step S332: Yes), the abnormality determining unit 357 determines that there is an abnormality in the pixel information which has been read by the timing generator 34 and the AFE unit 36, converted by the P/S conversion unit 39, and then transmitted (Step S334).

As in the third embodiment, the temperature sensor 382 may be provided in the CMOS imaging element 380 of the tip portion 305 and the abnormality determining unit 357 of the control device 340 may determine whether there is an abnormality in the pixel information which has been read by the timing generator 34 and the AFE unit 36, converted by the P/S conversion unit 39, and then transmitted, on the basis of the detection result of the temperature sensor 382.

In addition, the control circuit 335 may determine whether there is an abnormality in the pixel information which has been read by the timing generator 34 and the AFE unit 36, converted by the P/S conversion unit 39, and then transmitted, on the basis of whether the temperature of the board detected by the temperature sensor 382 is equal to or higher than a prescribed temperature. In this case, when the temperature of the board detected by the temperature sensor 382 is equal to or higher than the prescribed temperature, the control circuit 335 determines that there is an abnormality in the pixel information which has been read by the timing generator 34 and the AFE unit 36, converted by the P/S conversion unit 39, and then transmitted, and controls the light receiving unit 28, the timing generator 34, the AFE unit 36, and the P/S conversion unit 39 under the control conditions corresponding to the abnormal mode. In addition, the control circuit 335 notifies the control device 340 of information indicating that there is an abnormality in the pixel information which has been read by the timing generator 34 and the AFE unit 36, converted by the P/S conversion unit 39, and then transmitted. The control unit 355 receives the notice and directs the output unit 73 to output an alarm indicating that there is an abnormality in the pixel information.

Figure 17:
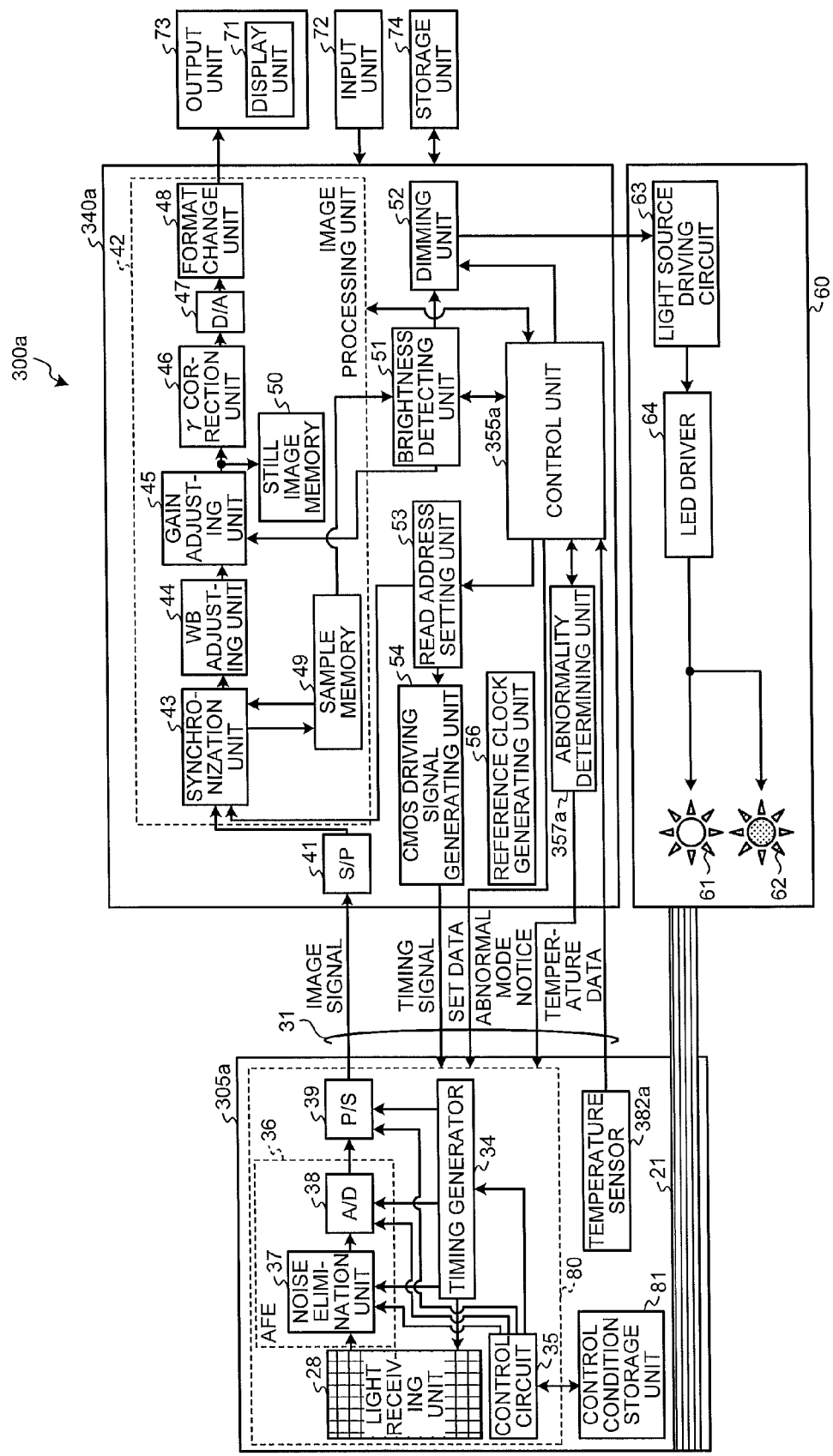
FIG. 17 is a block diagram illustrating another structure of the endoscope system according to the third embodiment.

In the third embodiment, the temperature sensor is provided in the board of the CMOS imaging element in the tip portion, but the invention is not limited thereto. As in an endoscope system 300a illustrated in FIG. 17, a temperature sensor 382a that is connected to a control unit 355a of a control device 340a may be provided in a tip portion 305a, separately from the CMOS imaging element 80. In this case, similarly to the abnormality determining unit 357, an abnormality determining unit 357a of the control device 340a determines whether there is an abnormality in the pixel information which has been read by the timing generator 34 and the AFE unit 36, converted by the P/S conversion unit 39, and then transmitted, on the basis of temperature data which is directly output from the temperature sensor 382a.

This embodiment is not limited to the endoscope system, but it may be applied to a capturing device, such as a digital camera, a digital single-lens reflex camera, a digital video camera, or a mobile phone with a camera. In this case, it is possible to improve efficiency.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging apparatus comprising:
    an imaging unit that is able to output, as pixel information, an electric signal that has been photoelectrically converted from a pixel arbitrarily designated as a target to be read from among a plurality of pixels for imaging;
    a reading unit that is provided on a board mounted with the imaging unit and reads pixel information from the pixel instructed as the target to be read in the imaging unit;
    an imaging-side control unit that is provided on the board and controls a pixel information output process by the imaging unit and a pixel information reading process by the reading unit;
    an image processing unit that generates an image from the pixel information read by the reading unit;
    a setting unit that is able to arbitrarily set the pixel to be read in the imaging unit;
    a control unit that changes the pixel to be read based on the setting by the setting unit;
    an abnormality determining unit that determines whether there is an abnormality in the pixel information read by the reading unit and outputs, upon determining that there is the abnormality in the pixel information read by the reading unit, to the imaging-side control unit, a notification signal for causing the imaging-side control unit to execute control on occurrence of the abnormality; and
    a light irradiating unit that irradiates light to an object, wherein the control unit controls, when the abnormality determining unit determines that there is the abnormality in the pixel information read by the reading unit, the light irradiating unit to reduce an amount of light irradiated by the light irradiating unit, wherein the imaging apparatus further comprises:
- a first signal conversion unit that converts a signal including the pixel information read by the reading unit from a parallel signal into a serial signal constituted in predetermined bit number units and outputs the serial signal;
- a transmitting unit that transmits the serial signal output by the first signal conversion unit; and
- a second signal conversion unit that converts the signal including the pixel information transmitted from the transmitting unit from the serial signal into a parallel signal and outputs the converted signal to the image processing unit,
- wherein the abnormality determining unit determines whether there is the abnormality based on whether the serial signal transmitted from the transmitting unit to the second signal conversion unit is constituted in predetermined bit number units.

2. The imaging apparatus according to claim 1, wherein the imaging-side control unit controls, upon receiving the notification signal output by the abnormality determining unit, the pixel information reading process by the reading unit such that a processed signal amount in the reading unit per unit time becomes less than a processed signal amount per unit time when normal.

3. The imaging apparatus according to claim 1, further comprising:
- a control condition storage unit that stores control conditions of the imaging unit and the reading unit for the occurrence of the abnormality,
- wherein the imaging-side control unit controls, upon receiving the notification signal output by the abnormality determining unit, the pixel information output process by the imaging unit and the pixel information reading process by the reading unit, based on the control conditions stored in the control condition storage unit.

4. The imaging apparatus according to claim 1, wherein the imaging-side control unit sets, upon receiving the notification signal output by the abnormality determining unit, some pixels extracted from all pixels of the imaging unit as pixels to be read in the imaging unit, and
the reading unit reads the pixel information from pixels of a light receiving unit that have been set by the imaging-side control unit as the pixels to be read.

5. The imaging apparatus according to claim 1, wherein the imaging-side control unit reduces, upon receiving the notification signal output from the abnormality determining unit, a reading speed of the pixel information by the reading unit.

6. The imaging apparatus according to claim 1, wherein the pixel information includes a brightness value,
the reading unit reads pixel information of a pixel on which light is incident and pixel information of a pixel on which light is not incident, and
the abnormality determining unit determines whether there is the abnormality based on a change in a brightness value of the pixel information of the pixel on which light is not incident read by the reading unit.

7. The imaging apparatus according to claim 1, further comprising:
- a first signal conversion unit that converts the pixel information read by the reading unit from an electric signal to an optical signal and outputs the optical signal;
- a transmitting unit that transmits the optical signal output from the first signal conversion unit; and
- a second signal conversion unit that converts the optical signal transmitted from the transmitting unit into an electric signal and outputs the converted signal to the image processing unit,
- wherein the abnormality determining unit determines whether there is the abnormality based on a change in signal intensity of the optical signal transmitted by the transmitting unit.

8. The imaging apparatus according to claim 1, wherein
the imaging-side control unit stores status information including information indicating whether there is an abnormality in the imaging unit and the reading unit and transmits the status information when instructed to transmit the status information, and
the abnormality determining unit instructs the imaging-side control unit to transmit the status information and determines whether there is the abnormality based on the status information transmitted from the imaging-side control unit.

9. The imaging apparatus according to claim 1, further comprising a temperature detecting unit that is provided on the board and detects a temperature of the board, wherein the abnormality determining unit determines whether there is the abnormality based on the temperature of the board detected by the temperature detecting unit.

10. The imaging apparatus according to claim 1, wherein
the imaging apparatus is an endoscope apparatus having a tip portion introduced into a body and a signal processing device, the tip portion and the signal processing device being connected by a transmitting unit,
the imaging unit, the reading unit, and the imaging-side control unit are provided in the tip portion, and
the image processing unit, the control unit, and the abnormality determining unit are provided in the signal processing device.

* * * * *